United States Patent [19]
Fletcher et al.

[11] Patent Number: 6,150,110
[45] Date of Patent: Nov. 21, 2000

[54] **HMGI(Y)-LAMA4\* FUSION ONCOGENE, ONCOPROTEIN AND METHODS OF USE**

[75] Inventors: Jonathan Fletcher, Brookline; Sheng Xiao, Boston, both of Mass.

[73] Assignee: The Brigham and Women's Hospital, Inc., Boston, Mass.

[21] Appl. No.: 09/258,373

[22] Filed: Feb. 26, 1999

Related U.S. Application Data

[60] Provisional application No. 60/076,401, Feb. 28, 1998.
[51] Int. Cl.$^7$ .............................. C12Q 1/68; C12N 15/00; C12N 5/00; C12N 1/20; C07H 21/04
[52] U.S. Cl. ........................... 435/6; 536/23.4; 536/23.5; 536/24.31; 536/24.33; 435/320.1; 435/325; 435/252.3; 436/503
[58] Field of Search ................................. 536/23.1, 23.5, 536/23.4, 24.31, 24.33, 24.5; 435/320.1, 325, 252.1; 800/13; 436/94

[56] References Cited

PUBLICATIONS

Verma et al. Nature 389: 239–242, especially p. 239, Sep. 1997.
Anderson et al. Nature 392: 25–30, especially pp. 25 and 30, Apr. 1997.
Crook In Basic Principles of Antisense Therapeutics, Springer–Verlag, Eds, New York, pp. 1–4, Jul. 1998.
Branch. Trends in Biochemical Sciences 23: 45–50, (see abstract; p. 49, paragraph bridging coluns 1 and 2; and p. 49, col. two first full paragraph), Sep. 1997.
Xiao et al. American Journal of Pathology 150(3): 901–910, (see p. 907, first sentence of first full paragraph; and p. 907, col. 2, first full paragraph; and p. 901, col. 2, first sentence of first full paragraph), Mar. 1997.
Wall. Theriogenology, 45: 57–68 See especially p. 61, last paragraph and p. 62, first paragraph, 1996.
Houdebine (Journal of Biotechnology 34:269–287, se especially p. 275, col. 1, 1st paragraph), 1994.
Mullins et al. (Journal of Clinical Investigation 98(11): S37–S40 See especially p. S39, 1996.
Kappel et al. (Current Opinion in Biotechnology, 3: 548–553, especially p. 549, col. 2, 3rd full paragraph, 1992.
Iivanainen et al (FEBS Lett. 365(2–3): 183–188, 1995 See Abstract and Figure 2, May 1995.
Xiao et al., "HBGI(Y) Activation by Chromosome 6p21 Rearrangements in Multilineage Mesenchymal Cells from Pulmonary Hamartoma," (1997) American Journal of Pathology, vol. 150, pp. 901–910.

*Primary Examiner*—Scott D. Priebe
*Assistant Examiner*—Richard Schnizer
*Attorney, Agent, or Firm*—Wolf, Greenfield & Sacks, P.C.

[57] ABSTRACT

An oncogene designated HMGI(Y)-LAMA4\* incorporates a HMGI(Y) domain fused through inversion and translocation to LAMA4\*, a novel gene transcript with a epidermal-growth-factor-like/zinc-finger-like motif. Molecular characterization of HMGI(Y)-LAMA4\* provides nucleic acid sequences and amino acid sequences useful for detection and treatment of certain tumors.

7 Claims, 3 Drawing Sheets

1   cttctggagcccttggaggggctccaaactgagaggggagggaagaccgcaggaaaggcg
61  gacctcagtgtctgaaaagccagcttagagtgggagggcctgggagtagaag(5'UTR-A)

1   caaactgaatcctgctttaattcaagcttgtggagaacaaagtcctacagaaacattcca
61  cagaattttctggaaaagagggatcacaacaaccctgtaaaaaggtgagaaggaagccag
121 gacagcgcagtccccagtcccgaacggccagggagaggaggtggcctagcgctggcgggg
181 ctcaccccaatccgtctgccttttgatgccgtact(5'UTR-B)
                                        ctgctggttgcgcacgcacctcggg
241 atactgcacacggagaggagggaaaataagcgaggcaccgccgcaccacgcggagaccta
301 cggagacccacagcgcccgagccctggaagagcactactggatgtcagcggagaaatggc
                                                              M  A
361 tttgagctcagcctggcgctcggttctgcctctgtggctcctctggagcgctgcctgctc
    L  S  S  A  W  R  S  V  L  P  L  W  L  L  W  S  A  A  C  S
421 ccgcgccgcgtccggggacgacaacgctttccttttgacattgaagggagctcagcggt
    R  A  A  S  G  D  D  N  A  F  P  F  D  I  E  G  S  S  A  V
481 tggcaggcaagacccgcctgagacgagcgaaccccgcgtggctctgggacgcctgccgcc
    G  R  Q  D  P  P  E  T  S  E  P  R  V  A  L  G  R  L  P  P
541 tgcggccgagaaatgcaatgctggattctttcacaccctgtcgggagaatgtgtgccctg
    A  A  E  K  Ⓒ  N  A  G  F  F  H  T  L  S  G  E  Ⓒ  V  P  Ⓒ
601 cgactgtaatggcaattccaacgagtgtttggacggctcaggatactgtgtgactactga
    D  Ⓒ  N  G  N  S  N  E  Ⓒ  L  D  G  S  G  Y  Ⓒ  V  T  T  D
661 cggagaagacccaggttttcagcttctaccctatcgttcattctcagctctcagggagc
    G  E  D  P  G  F  S  A  S  T  L  S  F  I  L  S  S  Q  G  A
721 cagagaagccagggctccaacatgaacacttcttgtagctcactgtcatgaccagtgttt
    R  E  A  R  A  P  T  *
781 cagtcagttctttcaggttgcctgacttacctcatttctctcatttcctgtaagcaacca
841 aaaataaaaggctttcttttatttcattttgtcttatttgcttttatcttgaaggcata
901 taagacctctgtatctgccttgttcaccttcaactgcttctaattcttcctcaattccag
961 tgtccaatgtcaatttgaaattaaaatttacagactgatttt

FIG. 3

HMGI(Y)-LAMA4* FUSION ONCOGENE, ONCOPROTEIN AND METHODS OF USE

RELATED APPLICATIONS

This application claims the benefit of priority under 35 U.S.C. Section 119 (e) to U.S. provisional application entitled "HMGI(Y)-LAMA4* Fusion Oncogene, Oncoprotein and Methods of Use", filed Feb. 28, 1998, Ser. No. 60/076,401.

FIELD OF THE INVENTION

The present invention relates to oncology and identification of oncogenes and oncoproteins and to diagnosis, prognosis and therapy associated with neoplasia.

DESCRIPTION OF RELATED ART

HMGI(Y) is a member of the high mobility group protein family which are alternative splicing products of the HMGI (Y) gene. HMGI(Y) encodes two proteins, resulting from alternative splicing, that bind AT-rich regions in the minor groove of DNA via amino acid A-T hook domains and thus participate in regulation of chromatin structure and gene expression. HMGI(Y) binds to DNA at many different chromosomal locations and, in so doing, changes the conformation (angle of bending) of the DNA. The DNA conformational alterations then enable adjacent transcription factors to function efficiently in gene regulation. HMGI(Y) proteins also regulate gene expression through direct physical interactions with transcription factors binding the DNA major groove.

Several reports have implicated HMGI(Y) expression in neoplastic progression. See, e.g., Ram et al., "Elevated high mobility group—1 (Y) gene expression is associated with progressive transformation of mouse mammary epithelial cells," *Cancer Res.* (1993) 53:2655–2660. HMGI(Y) is expressed at low levels in non-neoplastic human tissues, but is expressed abundantly in rapidly proliferating cells and in cancers which include prostate cancer, thyroid cancer and colorectal cancers. See, e.g., Johnson et al., "Expression of mRNA encoding mammalian chromosomal proteins HMG-I and HMG-Y during cellular proliferation," *Exp. Cell. Res.* (1990) 187:69–76; Tamimi et al., "Increased expression of high mobility group protein 1(Y) in high grade prostatic cancer determined by in situ hybridization," *Cancer Res.* (1993) 53:5512–5516; Chiappetta et al., "The expression of the high motility group HMG1(Y) proteins correlates with the malignant phenotype of human thyroid neoplasias", *Oncogene* (1995) 10:1307–1314; Fedele et al., "Human colorectal carcinomas express high levels of high mobility group HMG1(Y) proteins," *Cancer Res.* (1996) 56:1896–1901.

The HMGI(Y) gene maps to chromosome band 6p21. See Freidmann et al., "Organization, inducible expression, and chromosome localization of human HMG-I(Y) nonhistone protein gene," *Nucleic Acids Res.* (1993) 21:4259–4267. It has been reported that 25% of certain benign nodular growths known as pulmonary chondroid hamartomas (PCHs) contain clonal rearrangements involving the 6p21 chromosomal region. See, e.g., Fletcher et al., "Cytogenetic and histologic findings in 17 pulmonary chondroid hamartomas: evidence for a pathogenetic relationship with lipomas and leiomyomas," *Genes Chromosomes & Cancer* (1995) 12:220–223; Johansson et al., "Recombinations of chromosomal bands 6p21 and 14q24 characterize pulmonary hamartomas," *Br. J. Cancer* (1993) 67:1236–1241.

PCHs are typically less than 3 cm in diameter and are usually asymptomatic. They have not been reported to undergo malignant transformation or to recur after surgical removal. See Salminen, "Pulmonary hamartoma: a clinical study of 77 cases in a 21 year period and review of literature," *Eur. J. Cardiothorac. Surg.* (1990) 4:15–18. Recently, however, certain evidence has established a clonal neoplastic origin for PCH. See, e.g., Fletcher et al., supra; Johansson et al., supra. Both morphological and genetic findings suggest a pathogenetic relationship between PCHs, benign fat tumors (lipomas) and benign smooth muscle tumors (leiomyomas). Neoplastic progenitors in PCHs are primitive mesenchymal cells that differentiate into mature adipocytes, chondrocytes, and smooth muscle cells.

Despite reports relating to overexpression of HMGI-(Y) in cancer, potentially oncogenic HMGI(Y) mutations have not been found in primary human tumors nor in laboratory models of neoplasia. Indeed, since many genes are upregulated (overexpressed) in neoplastic cells, demonstration of upregulation does not prove that a gene plays a causal role in the neoplastic process. Therefore, it is unclear whether cancer HMGI-(Y) overexpression is an epiphenomenon related to rapid cell growth or a true oncogenetic event responsible for neoplastic progression. A definitive determination of the role of HMGI(Y) in connection with various cancers in which overexpression has been or may be demonstrated is highly desirable since such a determination would provide tools for early diagnosis and effective gene based treatments of such cancers.

Laminins are a family of protein adhesion factors which promote cellular attachment to tissue basement membranes. Laminins are large complex glycoproteins which contain various regions that are believed to regulate cell migration and proliferation. Laminins contain a number of functional domains which include one that binds to type IV collagen, one to heparin sulfate, and one or more that bind to laminin receptor proteins on the surface of cells. See, Alberts et al., *The Molecular Biology of the Cell*, 2d ed., Garland Publishing (1989) pg. 819. Many varieties of laminin proteins have been identified, and some varieties are overexpressed in certain types of human tumors. One laminin protein, designated LAMA4(6.2 kb) was previously characterized. However, there has been no evidence that laminin proteins have oncogenic roles, i.e., there has been no evidence that laminins are activated by mutations in a manner which promotes neoplastic transformation.

The search for mechanisms underlying cancer and oncogenesis is ongoing. Understanding tumorigenesis and the reasons for uncontrolled and/or rapid cell proliferation will help researchers develop tools for early detection, diagnosis and aggressive treatment of neoplasias. Molecular characterization of oncogenic events which lead to upregulation of HMGI(Y) would provide an effective tool for diagnostic and therapeutic modalities relating to tumorigenesis and neoplasias which are associated with increased HMGI(Y) expression.

SUMMARY OF THE INVENTION

In accordance with the present invention, an oncogene designated HMGI(Y)-LAMA4* has been identified which incorporates a LAMA4* gene fused through translocation to HMGI(Y), and is associated with certain tumors. In accordance therewith, an isolated HMGI(Y)-LAMA4* nucleic acid is provided. As used herein, a HMGI(Y)-LAMA4* nucleic acid refers to a nucleic acid which contains, from 5' to 3', a HMGI(Y)-derived nucleic acid sequence and a LAMA4*-derived nucleic acid sequence. The exact number of nucleotides in the HMGI(Y)-derived nucleic acid sequence and the LAMA4*-derived nucleic acid sequence can vary, provided that the HMGI(Y)-LAMA4* nucleic acid contains a sufficient number of nucleotides from the respective source genes to identify the HMGI(Y)-LAMA4* nucleic acid as a unique nucleic acid sequence that is derived from each of these source genes.

The locus in the HMGI(Y)-LAMA4* nucleic acid which marks the boundary between the sequence derived from the HMGI(Y) nucleic acid and the sequence derived from the LAMA4* nucleic acid is referred to as the "translocation fusion juncture". Accordingly, the HMGI(Y)-LAMA4* nucleic acids of the invention also are said to contain a "HMGI(Y)-LAMA4* fusion sequence", i.e., the minimum nucleotide sequence which identifies the HMGI(Y)-LAMA4* nucleic acid as a unique nucleic acid sequence that is derived from each of the source genes. The translation product of a HMGI(Y)-LAMA4* fusion sequence is referred to as a HMGI(Y)-LAMA4* polypeptide fusion sequence. Accordingly, the HMGI(Y)-LAMA4* polypeptides of the invention also are said to contain a "HMGI(Y)-LAMA4* polypeptide fusion sequence", i.e., the minimum amino acid sequence which identifies the HMGI(Y)-LAMA4* polypeptide as a unique polypeptide that includes an amino acid sequence coded for by each of the source genes.

According to one aspect of the invention, an isolated HMGI(Y)-LAMA4* nucleic acid is provided which is selected from the following nucleic acid molecules:

(a) a nucleic acid molecule which hybridizes under stringent conditions to a nucleic acid molecule consisting of a nucleic acid of SEQ ID NO:2 and which codes for a HMGI(Y)-LAMA4* polypeptide;

(b) deletions, additions and substitutions of (a) which code for a respective HMGI(Y)-LAMA4* polypeptide;

(c) a nucleic acid molecule that differs from the nucleic acid molecules of (a) or (b) in codon sequence due to the degeneracy of the genetic code; and (d) complements of (a), (b) or (c).

The preferred HMGI(Y)-LAMA4* nucleic acid molecules have a sequence selected from the group consisting of SEQ ID NO:2 and SEQ ID NO:1 (GGCAGACCCAAAAAACTGAAATGCAATGCT). SEQ ID NO:2 codes for the HMGI(Y)-LAMA4* polypeptide of SEQ ID NO:3; SEQ ID NO:1 codes for the HMGI(Y)-LAMA4* polypeptide of SEQ ID NO:4 (GRPKKLKCNA) which is also contained within the sequence depicted in SEQ ID NO:3.

According to yet another aspect of the invention, an isolated HMGI(Y)-LAMA4* nucleic acid molecule is provided which is selected from the group consisting of:

(a) a unique fragment of a nucleic acid molecule selected from the group consisting of SEQ ID NO:1 and SEQ ID NO:2 (of sufficient length to represent a sequence unique within the human genome); and (b) complements of (a), provided that the unique fragment includes a sequence of contiguous nucleotides which excludes a sequence selected from the group consisting of: (1) sequences having the SEQ ID NOs or GenBank accession numbers of Tables 1a and 1b or other previously published sequences as of the date of invention or the filing date of this application, (2) complements of (1), and (3) fragments of (1) and (2).

According to another aspect of the invention, an expression vector comprising the nucleic acid molecules disclosed herein operably linked to a promoter are provided. Host cells containing (e.g., transformed or transfected with) said expression vectors also are provided. In certain preferred embodiments, the host cells are eukaryotic cells.

The isolated HMGI(Y)-LAMA4* nucleic acid molecules disclosed herein have various utilities, including their use as probes and primers as diagnostic reagents for identifying the presence of HMGI(Y)-LAMA4* nucleic acids in biological or other samples, and as agents for generating HMGI(Y)-LAMA4* polypeptides and HMGI(Y)-LAMA4* binding agents (agents such as antibodies which selectively bind to a HMGI(Y)-LAMA4* nucleic acid or to a HMGI(Y)-LAMA4* polypeptide) that can be used as reagents in diagnostic and therapeutic assays to identify the presence, absence, and/or amounts of a HMGI(Y)-LAMA4* nucleic acid or polypeptide in a biological or other sample. Thus, the HMGI(Y)-LAMA4* nucleic acids, polypeptides, and binding agents of the invention can be used, inter alia, in the diagnosis or treatment of conditions characterized by the presence of aberrant levels of a HMGI(Y)-LAMA4* nucleic acid or of a HMGI(Y)-LAMA4* polypeptide.

According to yet another aspect of the invention, an isolated HMGI(Y)-LAMA4* polypeptide is provided. The isolated HMGI(Y)-LAMA4* polypeptide molecule is encoded by one or more HMGI(Y)-LAMA4* nucleic acid molecules of the invention. Preferably, the HMGI(Y)-LAMA4* polypeptide is selected from the group consisting of the polypeptides having SEQ ID NO:3 and SEQ ID NO:4. More preferably, the HMGI(Y)-LAMA4* polypeptide is SEQ ID NO:4 or a unique fragment of SEQ ID NO:3 which contains at least two, preferably three, and, more preferably, four amino acids from the LAMA4*-and HMGI(Y)-derived polypeptide sequences.

According to another aspect of the invention, isolated HMGI(Y)-LAMA4* binding agents (e.g., binding polypeptides such as antibodies) are provided which selectively bind to a HMGI(Y)-LAMA4* nucleic acid molecule or to a HMGI(Y)-LAMA4* polypeptide encoded by the isolated nucleic acid molecules of the invention. Preferably, the isolated binding agents selectively bind to a nucleic acid having a sequence selected from the group consisting of SEQ ID NO:1 and SEQ ID NO:2; or to a polypeptide having a sequence selected from the group consisting of SEQ ID NO:3 and SEQ ID NO:4, or to unique fragments of the foregoing nucleic acids and polypeptides. In the preferred embodiments, the isolated binding polypeptides include antibodies and fragments of antibodies (e.g., Fab, F(ab)$_2$, Fd and antibody fragments which include a CDR3 region which binds selectively to the HMGI(Y)-LAMA4* nucleic acid or polypeptide). Accordingly, throughout this application, the term "antibody" is meant to embrace antibody fragments which selectively bind to the target antigen. Preferably, the antibodies for human therapeutic applications are human antibodies.

According to another aspect of the invention, a method of identifying certain tumors (e.g., hamartoma) is provided. The method includes obtaining tissue or fluid from a patient and analyzing the tissue or fluid for the presence of a nucleic acid sequence containing a HMGI(Y)-LAMA4* nucleic acid molecule (e.g., SEQ ID NO:1 or SEQ ID NO:2), a HMGI(Y)-LAMA4* polypeptide (e.g., SEQ ID NO:3 or SEQ ID NO:4), or unique fragments of the foregoing nucleic acid molecules and polypeptides, wherein the presence of such a nucleic acid sequence or polypeptide identifies certain tumors.

According to still another aspect of the invention, a method of identifying the presence of a HMGI(Y)-LAMA4* nucleic acid in a sample is provided. The method involves contacting the sample with at least two nucleic acid amplification primers, wherein a first amplification primer hybridizes to the HMGI(Y) nucleic acid sequence and a second amplification primer hybridizes to the LAMA4* nucleic acid sequence; amplifying the primed sequences in the sample which hybridize to the two primers; and detecting the presence of amplified nucleic acid sequence in the sample which contains the HMGI(Y)-LAMA4* nucleic acid sequence.

According to yet another aspect of the invention, a method of identifying the presence of HMGI(Y)-LAMA4* nucleic acid sequence in a sample is provided. The method involves contacting the sample with at least two nucleic acid probes, wherein a first probe hybridizes to the HMGI(Y) nucleic acid sequence and a second probe hybridizes to the LAMA4* nucleic acid sequence; and detecting the presence of a nucleic acid sequence in the sample which hybridizes to both the first probe (HMGI(Y)-specific probe) and to the second probe (LAMA4*-specific probe).

According to a further aspect of the invention, a method of identifying the presence of the HMGI(Y)-LAMA4* fusion sequence in a sample is provided. The method involves contacting the sample with a nucleic acid probe which hybridizes to the locus of the junction (i.e., the translocation fusion juncture) between the HMGI(Y) portion and the LAMA4* portion of the HMGI(Y)-LAMA4* fusion sequence; and detecting the presence of a nucleic acid sequence in the sample which hybridizes to the probe.

According to yet another aspect of the invention, a method of identifying the presence of HMGI(Y)-LAMA4* polypeptide in a sample is provided. The method involves contacting the sample with at least two binding agents (e.g., an antibody), wherein a first binding agent selectively binds to HMGI(Y) and a second binding agent selectively binds to LAMA4*; and detecting the presence of a polypeptide in the sample which binds both the first and the second binding agents.

According to a further aspect of the invention, a method of identifying the presence of HMGI(Y)-LAMA4* polypeptide fusion sequence in a sample is provided. The method involves contacting the sample with a binding agent (e.g., an antibody) which binds selectively to the HMGI(Y)-LAMA4* polypeptide fusion sequence, and detecting the presence of a polypeptide in the sample which selectively binds to the binding agent.

According to another aspect of the invention, a pharmaceutical composition containing a therapeutically effective amount of an isolated HMGI(Y)-LAMA4* nucleic acid, an isolated HMGI(Y)-LAMA4* polypeptide, or an isolated HMGI(Y)-LAMA4* binding agent in a pharmaceutically acceptable carrier is provided. The pharmaceutical compositions are useful in accordance with the therapeutic methods, including the diagnostic imaging applications, disclosed herein.

Thus, according to a further aspect of the invention, a method of locating cells containing a HMGI(Y)-LAMA4* polypeptide (e.g., SEQ ID NO:3 or SEQ ID NO:4) in a patient is provided. The method involves providing a binding agent to which is coupled a detectable tag (e.g., a radio labeled antibody) which selectively binds to the HMGI(Y)-LAMA4* polypeptide fusion sequence; injecting the labeled binding agent into a patient suspected of having cells containing the HMGI(Y)-LAMA4* polypeptide; and observing the locus of label (e.g., radioactivity) in the patient.

According to another aspect of the invention, a method of delivering a toxic substance to cells in a patient containing a HMGI(Y)-LAMA4* polypeptide is provided. The method involves providing a toxin-conjugated binding agent (e.g., a toxin-conjugated antibody or antibody fragment) that selectively binds to the HMGI(Y)-LAMA4* polypeptide fusion sequence; and injecting the toxin-conjugated binding agent (e.g., toxin-conjugated antibody) into the patient suspected of having cells containing a HMGI(Y)-LAMA4* polypeptide.

The invention also discloses the nucleic acid and predicted amino acid sequence for a novel gene, referred to herein as LAMA4*. SEQ ID NO:7 is the nucleotide sequence of LAMA4* cDNA. SEQ ID NO:8 is the amino acid sequence of LAMA4* protein. As described above, sequences derived from the LAMA4* nucleic acid sequence are contained within the HMGI(Y)-LAMA4* nucleic acid molecules of the invention. The LAMA4* cDNA sequence is presented in SEQ ID NO:7; the LAMA4* amino acid sequence is presented in SEQ ID NO:8 Accordingly, the invention also provides an isolated LAMA4* nucleic acid molecule. These isolated nucleic acid molecules of the invention are selected from the following nucleic acid molecules:

(a) a nucleic acid molecule which hybridizes under stringent conditions to a nucleic acid molecule consisting of a nucleic acid of SEQ ID NO:7 and which codes for a LAMA4* polypeptide;

(b) deletions, additions and substitutions of (a) which code for a respective LAMA4* polypeptide;

(c) a nucleic acid molecule that differs from the nucleic acid molecules of (a) or (b) in codon sequence due to the degeneracy of the genetic code, and (d) complements of (a), (b) or (c). Exemplary LAMA4* nucleic acid molecules have SEQ ID NO:7 or have nucleic acid sequences which encode SEQ ID NO:8.

According to yet another aspect of the invention, an isolated LAMA4* nucleic acid molecule is provided which is selected from the group consisting of:

(a) a unique fragment of a nucleic acid molecule selected from the group consisting of SEQ ID NO:7 (of sufficient length to represent a sequence unique within the human genome); and (b) complements of (a), provided that the unique fragment includes a sequence of contiguous nucleotides which excludes a sequence selected from the group consisting of: (1) sequences having the SEQ ID NOs or GenBank accession numbers of Table 2 or other previously published sequences as of the date of invention or the filing date of this application, (2) complements of (1), and (3) fragments of (1) and (2).

According to another aspect of the invention, expression vectors comprising the LAMA4* nucleic acid molecules disclosed herein operably linked to a promoter, and host cells containing said expression vectors also are provided.

The isolated LAMA4* nucleic acid molecules disclosed herein have various utilities, including their use as probes and primers as diagnostic reagents for identifying the presence of LAMA4* nucleic acids in biological or other samples, and as agents for generating LAMA4* polypeptides and LAMA4* binding agents (e.g., antibodies) that can be used as reagents in diagnostic and therapeutic assays to identify the presence, absence, and/or amounts of a LAMA4* nucleic acid or polypeptide in a biological or other sample. Thus, the foregoing nucleic acids, polypeptides, and binding agents can be used, inter alia, in the diagnosis or treatment of conditions characterized by the expression or presence of a LAMA4* nucleic acid or polypeptide.

According to yet another aspect of the invention, an isolated LAMA4* polypeptide is provided. The isolated LAMA4* polypeptide molecule is encoded by one or more LAMA4* nucleic acid molecules of the invention.

According to another aspect of the invention, isolated LAMA4* binding agents (e.g., binding polypeptides such as antibodies) are provided which selectively bind to a LAMA4* nucleic acid molecule or to a LAMA4* polypeptide encoded by the isolated nucleic acid molecules of the invention. Preferably, the isolated binding agents selectively bind to a nucleic acid of SEQ ID NO:7 or to a polypeptide of SEQ ID NO:8, or to unique fragments of the foregoing nucleic acids and polypeptides. In the preferred embodiments, the isolated binding polypeptides include antibodies and fragments of antibodies (e.g., Fab, F(ab)$_2$, Fd and antibody fragments which include a CDR3 region which binds selectively to a LAMA4* nucleic acid or polypeptide). As used herein, the term antibody is meant to include such fragments. Preferably, the antibodies for human therapeutic applications are human, or humanized antibodies that are non-antigenic in humans.

According to another aspect of the invention, a method of identifying certain tumors is provided. The method includes obtaining tissue or fluid from a patient and analyzing the tissue or fluid for the presence of a nucleic acid sequence containing a LAMA4* nucleic acid molecule (e.g., SEQ ID NO:7), a LAMA4* polypeptide (e.g., SEQ ID NO:8), or unique fragments thereof wherein the presence of such a nucleic acid sequence or polypeptide identifies certain tumors.

According to still another aspect of the invention, a method of identifying the presence of LAMA4* nucleic acid sequence in a sample is provided. The method involves contacting the sample with at least two nucleic acid amplification primers, wherein the first primer hybridizes to a first unique sequence within the LAMA4* nucleic acid sequence and the second primer hybridizes to a second unique sequence within the LAMA4* nucleic acid sequence; amplifying the primed sequences in the sample which hybridizes to the two primers; and detecting the presence of amplified nucleic acid sequence in the sample which contains the LAMA4* nucleic acid sequence.

According to yet another aspect of the invention, a method of identifying the presence of a LAMA4* nucleic acid sequence in a sample is provided. The method involves contacting the sample with at least two nucleic acid probes, wherein the first probe hybridizes to a first unique sequence within the LAMA4* nucleic acid sequence and the second probe hybridizes to a second unique sequence within the LAMA4* nucleic acid sequence; and detecting the presence of a nucleic acid sequence in the sample which hybridizes to both the first probe and to the second probe.

According to yet another aspect of the invention, a method of identifying the presence of a LAMA4* polypeptide in a sample is provided. The method involves contacting the sample with at least two binding agents (e.g., an antibody), wherein the first binding agent selectively binds to a first unique sequence within the LAMA4* polypeptide and the second binding agent selectively binds to a second unique sequence within the LAMA4* polypeptide; and detecting the presence of a protein in the sample to which each of the first and the second binding agents bind.

According to another aspect of the invention, a pharmaceutical composition containing a therapeutically effective amount of an isolated LAMA4* nucleic acid, an isolated LAMA4* polypeptide, or an isolated LAMA4* binding agent in a pharmaceutically acceptable carrier also is provided. The pharmaceutical compositions are useful in accordance with therapeutic methods disclosed herein.

According to a further aspect of the invention, a method of locating cells containing a LAMA4* polypeptide in a patient is provided. The method involves providing a binding agent to which is coupled a detectable tag (e.g., a radiolabeled antibody) which selectively binds to the LAMA4* polypeptide; injecting the labeled binding agent into a patient suspected of having cells containing a LAMA4* polypeptide; and observing the locus of detectable tag (e.g., by detecting radioactivity) in the patient.

According to another aspect of the invention, a method of delivering a toxic substance to cells in a patient containing a LAMA4* polypeptide is provided. The method involves providing a toxin-conjugated binding agent (e.g., a toxin-conjugated antibody) that selectively binds to a LAMA4* polypeptide; and injecting the toxin-conjugated binding agent into the patient suspected of having cells containing a LAMA4* polypeptide.

In summary, the invention provides isolated LAMA4* nucleic acid molecules and isolated HMGI(Y)-LAMA4* nucleic acid molecules, unique fragments thereof, expression vectors containing the foregoing, and host cells containing the foregoing. The invention also provides isolated LAMA4* polypeptides and isolated HMGI(Y)-LAMA4* polypeptides, binding agents which selectively bind such nucleic acids and polypeptides, including antibodies, and pharmaceutical compositions containing the foregoing molecules. The compositions of the invention can be used, inter alia, in the diagnosis or treatment of conditions characterized by the aberrant expression levels and/or the presence of a LAMA4* or HMGI(Y)-LAMA4* nucleic acid or polypeptide.

Expression and/or translation of HMGI(Y)-LAMA4* and/or of LAMA4* may be reduced or disrupted by antisense nucleotides or ribozymes. Furthermore, neoplasia may be produced by introducing HMGI(Y)-LAMA4* or LAMA4* into a cell and transgenic animals including HMGI(Y)-LAMA4* and LAMA4* are provided.

BRIEF DESCRIPTION OF THE DRAWINGS

FIG. 3 depicts cDNA and corresponding amino acid sequence for LAMA4* 5'UTR-A and 5'UTR-B.

ABBREVIATED SEQUENCE LISTING

Figure 1:
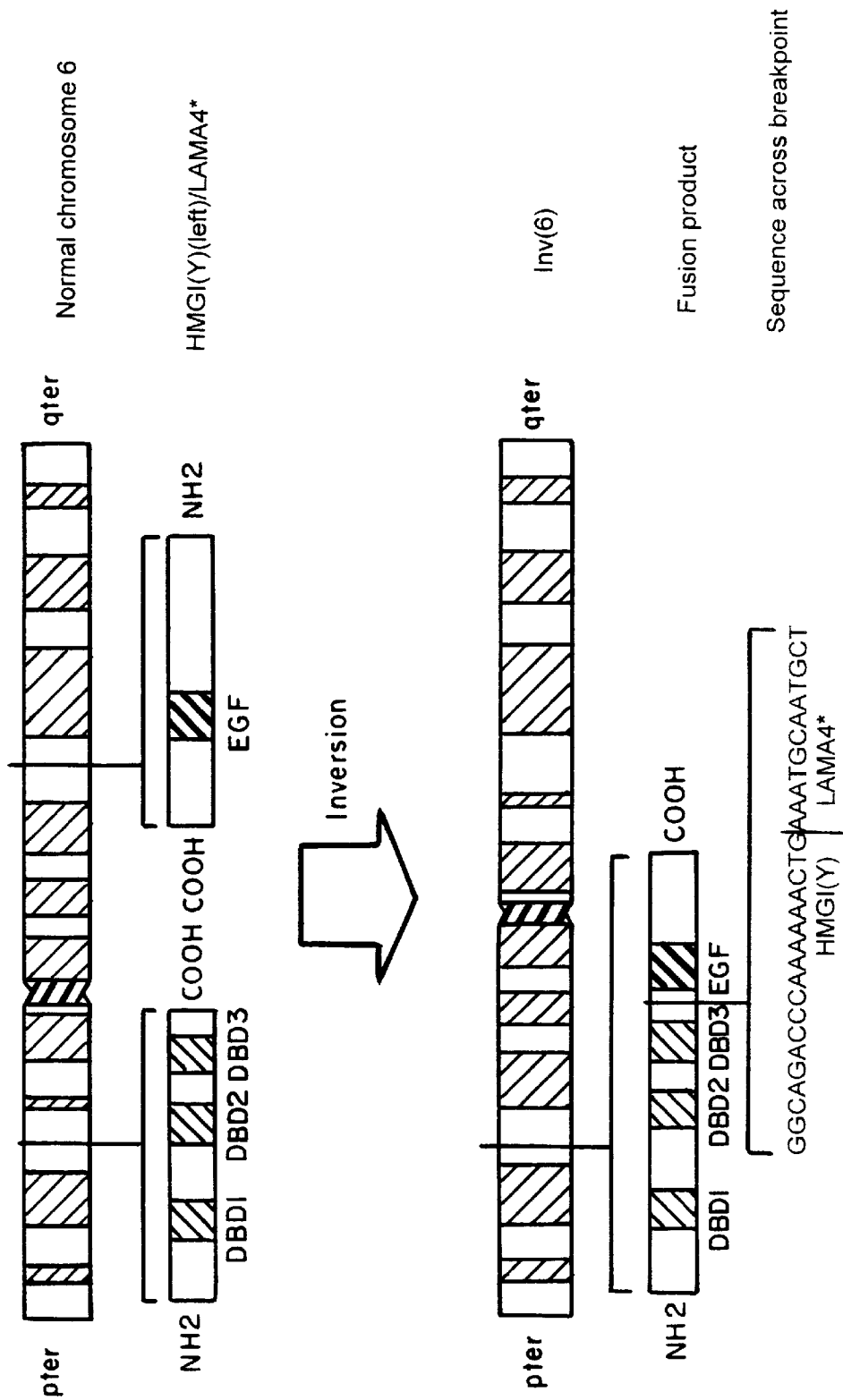
FIG. 1 depicts an ideogram showing chromosome 6 inversion and translocation resulting in fusion of HMGI(Y) and LAMA4*.

SEQ ID NO:1 is the nucleotide sequence including and surrounding the translocation fusion juncture in the HMGI (Y)-LAMA4* DNA.

SEQ ID NO:2 is the nucleotide sequence of HMGI(Y)-LAMA4* cDNA.

SEQ ID NO:3 is the amino acid sequence of HMGI(Y)-LAMA4* protein.

SEQ ID NO:4 is the amino acid sequence including and surrounding the translocation fusion juncture in the HMGI (Y)-LAMA4* protein.

SEQ ID NO:5 is the nucleotide sequence designated LAMA4* 5'UTR-A.

SEQ ID NO:6 is the nucleotide sequence designated LAMA4* 5'UTR-B.

SEQ ID NO:7 is the nucleotide sequence of LAMA4* cDNA.

SEQ ID NO:8 is the amino acid sequence of LAMA4* protein.

SEQ ID NO:9 is the nucleotide sequence of a forward amplification primer which hybridizes to HMGI(Y) DNA and is used to amplify SEQ ID NO:1.

SEQ ID NO:10 is the nucleotide sequence of a reverse amplification primer which hybridizes to HMGI(Y) DNA.

SEQ ID NO:11 is the nucleotide sequence of an oligo dT amplification primer used to reverse transcribe RNA.

SEQ ID NO:12 is the nucleotide sequence of a forward amplification primer which hybridizes to HMGI(Y) exon 5 cDNA and is used for RT-PCR.

SEQ ID NO:13 is the nucleotide sequence of a reverse amplification primer designated Q0 which is used to amplify SEQ ID NO:1.

SEQ ID NO:14 is the nucleotide sequence of a forward amplification primer which hybridizes to HMGI(Y) DNA.

SEQ ID NO:15 is the nucleotide sequence of a reverse amplification primer designated Q1.

SEQ ID NO:16 is the nucleotide sequence of a reverse amplification primer which hybridizes to LAMA4* DNA.

SEQ ID NO:17 is the nucleotide sequence of a forward amplification primer which hybridizes to HMGI(Y) DNA.

SEQ ID NO:18 is the nucleotide sequence of a reverse amplification primer which hybridizes to LAMA4* DNA.

SEQ ID NO:19 is the nucleotide sequence of a reverse amplification primer which hybridizes to LAMA4* DNA.

SEQ ID NO:20 is the nucleotide sequence of a probe which hybridizes to LAMA4* DNA.

SEQ ID NO:21 is the nucleotide sequence of HMGI(Y) cDNA.

SEQ ID NO:22 is the amino acid sequence of HIMGI(Y) protein.

DESCRIPTION OF PREFERRED EMBODIMENTS

The present invention involves a definitive demonstration of an oncogenic role for the HMGI(Y) gene in connection with a fusion transcript designated HMGI(Y)-LAMA4* and its molecular characterization. Such characterization revealed a novel laminin transcript designated LAMA4* which is much shorter than previously described LAMA4 transcripts. Prior to elucidation of LAMA4*, as with HMGI (Y), laminins had not been shown to be targeted by oncogenic mutations. Molecular characterization of the HMGI (Y)-LAMA4* oncogene and oncoprotein encoded thereby provides the ability to identify the location of tumors containing the oncogene or oncoprotein.

In accordance with present invention, it was determined that an intragenic rearrangement involving the chromosome band 6p21 HMGI(Y) gene in PCHs was present and, more particularly, an intragenic fusion was found juxtaposing HMGI(Y) A-T hook DNA binding domains with a LAMA4* epidermal growth factor (EGF)-like/zinc finger motif. This determination was made by using fluorescence in-situ hybridization (FISH) mapping of yeast artificial chromosome (YAC) clones which were centromeric and telomeric to the breakpoint in chromosome band 6p2 1, followed by Southern blot and Northern blot expression studies. Characterization of the HMGI(Y)-LAMA4* fusion transcripts was accomplished by reverse transcribing RNA with subsequent amplification of cDNA and sequencing. 5' rapid amplification of cDNA ends (RACE) was utilized to elucidate LAMA4* followed by sequencing and Northern blot expression studies.

Thus, in accordance with the present invention, an oncogene designated HMGI(Y)-LAMA4* has been identified which incorporates an HMGI(Y) domain fused through translocation to a LAMA4* domain and is associated with certain tumors. In accordance therewith, an isolated HMGI (Y)-LAMA4* nucleic acid is provided. As used herein, a "HMGI(Y)-LAMA4* nucleic acid", refers to a nucleic acid which contains, from 5' to 3', a HMGI(Y)-derived nucleic acid sequence and a LAMA4*-derived nucleic acid sequence. The exact number of nucleotides in the HMGI (Y)-derived nucleic acid sequence and the LAMA4*-derived nucleic acid sequence can vary, provided that the HMGI(Y)-LAMA4* nucleic acid contains a sufficient number of nucleotides from the respective source genes to identify the HMGI(Y)-LAMA4* nucleic acid as a unique nucleic acid sequence that is derived from each of these source genes.

The locus in the HMGl(Y)-LAMA4* nucleic acid which marks the boundary between the sequence derived from the HMGI(Y) nucleic acid and the sequence derived from the LAMA4* nucleic acid is referred to as the "translocation fusion juncture". Accordingly, the HMGIfY)-LAMA4* nucleic acids of the invention also are said to contain a "HMGI(Y)-LAMA4* fusion sequence", i.e., the minimum nucleotide sequence which identifies the HMGI(Y)-LAMA4* nucleic acid as a unique nucleic acid sequence that is derived from each of the source genes. The translation product of a HMGI(Y)-LAMA4* fusion sequence is referred to as a HMGI(Y)-LAMA4* polypeptide fusion sequence. Accordingly, the HMGI(Y)-LAMA4* polypeptides of the invention also are said to contain an "HMGI (Y)-LAMA4* polypeptide fusion sequence", i.e., the minimum amino acid sequence which identifies the HMGI(Y)-LAMA4* polypeptide as a unique polypeptide that includes an amino acid sequence coded for by each of the source genes.

Both the HMGI(Y) gene and the LAMA4* gene are located on chromosome 6. FIG. 1 is an ideogram which graphically shows the location of HMGI(Y) and LAMA4* on chromosome 6 along with a further representation of translocation and inversion yielding the HMGI(Y)-LAMA4* fusion product. The amino terminus of HMGI(Y) is fused at the carboxy terminus of LAMA4*. The sequence across the breakpoint, i.e., GGCAGACCCAAAAAACT-GAAATGCAATGCT (SEQ ID NO:1) is shown with a vertical line marking the fusion site. The HMGI(Y)-LAMA4* fusion nucleic acid molecule shown as SEQ ID NO:2 and derived from reverse transcribing RNA as described below is a 920 bp sequence. The translocation breakpoint (i.e., translocation fusion juncture) in SEQ ID NO:2 denoting the boundary between HMGI(Y) and LAMA4* nucleotide sequence occurs between nucleotides 468 and 469. The HMGI(Y)-LAMA4* amino acid sequence shown in SEQ ID NO:3 is 143 amino acids long with the breakpoint between the HMGI(Y) and the LAMA4* amino acid sequences occurring between amino acids 79 and 80. An isolated nucleic acid sequence which encodes the LAMA4* polypeptide is shown in SEQ ID NO:7 and the corresponding amino acid sequence of LAMA4* is shown in SEQ ID NO:8. The novel LAMA4* cDNA contains a 3' end with no homologies to laminin family members. Two LAMA4* cDNA sequences with identical coding regions but different 5' untranslated regions (UTR) were uncovered. The respective untranslated regions are designated LAMA4* 5'UTR-A (SEQ ID NO:5) and LAMA4* 5'UTR-B (SEQ ID NO:6). The HMGI(Y)-LAMA4* oncogene is described in Xiao, et al., "HMGI(Y) Activation by Chromosome 6p21 Rearrangements in Multilineage Mesenchymal Cells from Pulmonary Hamartoma," *Am. J. Path.* (March 1997) 150: 901–910, incorporated herein by reference.

According to one aspect of the invention, an isolated HMGI(Y)-LAMA4* nucleic acid is provided which is selected from the following nucleic acid molecules:

(a) a nucleic acid molecule which hybridizes under stringent conditions to a nucleic acid molecule consisting of a nucleic acid of SEQ ID NO:2 and which codes for a HMGI(Y)-LAMA4* polypeptide;

(b) deletions, additions and substitutions of (a) which code for a respective HMGI(Y)-LAMA4* polypeptide;

(c) a nucleic acid molecule that differs from the nucleic acid molecules of (a) or (b) in codon sequence due to the degeneracy of the genetic code; and (d) complements of (a), (b) or (c).

The preferred HMGI(Y)-LAMA4* nucleic acid molecules have a sequence selected from the group consisting of SEQ ID NO:1 (GGCAGACCCAAAAAACTGAAATGCAATGCT) and SEQ ID NO:2. SEQ ID NO:2 codes for the HMGI(Y)-LAMA4* polypeptide of SEQ ID NO:3; SEQ ID NO:1 codes for the HMGI(Y)-LAMA4* polypeptide of SEQ ID NO:4 (GRPKKLKCNA) which is also contained within the sequence depicted in SEQ ID NO:3.

According to yet another aspect of the invention, an isolated HMGI(Y)-LAMA4* nucleic acid molecule is provided which is selected from the group consisting of:

(a) a unique fragment of a nucleic acid molecule selected from the group consisting of SEQ ID NO:1 and SEQ ID NO:2 (of sufficient length to represent a sequence unique within the human genome); and (b) complements of (a), provided that the unique fragment includes a sequence of contiguous nucleotides which excludes a sequence selected from the group consisting of: (1) sequences having the SEQ ID NOs or GenBank accession numbers of Tables 1a and 1b, or other previously published sequences as of the date of invention or the filing date of this application, (2) complements of (1), and (3) unique fragments of (1) and (2).

In certain embodiments, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In other embodiments, the unique fragment has a size selected from the group consisting of at least: 8 nucleotides, 10 nucleotides, 12 nucleotides, 14 nucleotides, 16 nucleotides, 18 nucleotides, 20 nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect of the invention, expression vectors comprising the HMGI(Y)-LAMA4* nucleic acid molecules disclosed herein operably joined to a promoter and host cells containing said expression vectors are provided. In certain preferred embodiments, the host cells are eukaryotic cells. As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Insertion of any of the nucleic acid sequences described herein into an appropriate vector allows production of large quantities of such sequences. Indeed, vectors, methods for inserting nucleic acids into vectors, and use of such vectors for production of desired nucleic acids, peptides and proteins are well known to those with skill in the art. Thus, the nucleic acid sequences disclosed herein can also be inserted into cloning and/or expression vectors to produce peptides and proteins according to the present invention.

Procedures and materials for preparation of replicable vectors, transformation of host cells with vectors, and host cell expression of polypeptides are described in Maniatis et al., *Molecular Cloning: A Laboratory Manual*, Cold Spring Harbor (1982) incorporated herein by reference. Any replicable vector known to those with skill in the art may be used to clone or amplify HMGI(Y)-LAMA4* or LAMA4* nucleic acids and/or to produce polypeptides encoded thereby. For example, suitable vectors include plasmids, phages, cosmids and artificial chromosomes. For example, bacteriophage lambda may be a useful cloning vector. This phage can accept pieces of foreign DNA up to about 20,000 base pairs in length. The lambda phage genome is a linear double stranded DNA molecule with single stranded complementary (cohesive) ends which can hybridize with each other when inside an infected host cell. The lambda DNA is cut with a restriction endonuclease and the foreign DNA, e.g., the DNA to be cloned, is ligated to the phage DNA fragments. The resulting recombinant molecule is then packaged into infective phage particles. Host cells are infected with the phage particles containing the recombinant DNA. The phage DNA replicates in the host cell to produce many copies of the desired DNA sequence.

Cosmids are hybrid plasmid/bacteriophage vectors which can be used to clone DNA fragments of about 40,000 base pairs. Cosmids have one or more DNA sequences called "cos" sites derived from bacteriophage lambda for packaging lambda DNA into infective phage particles. Two cosmids are ligated to the DNA to be cloned. The resulting molecule is packaged into infective lambda phage particles and transfected into bacteria host cells. When the cosmids are inside the host cell they behave like plasmids and multiply under the control of a plasmid origin of replication. The origin of replication is a sequence of DNA which allows a plasmid to multiply within a host cell.

Yeast artificial chromosome vectors (YAC) are similar to plasmids but allow for the incorporation of much larger DNA sequences of about 400,000 base pairs. The yeast artificial chromosomes contain sequences for replication in yeast. The yeast artificial chromosome containing the DNA to be cloned is transformed into yeast cells where it replicates thereby producing many copies of the desired DNA sequence. Where phage, cosmids or yeast artificial chromosomes are employed as cloning vectors, expression of the fusion protein or LAMA4* may be obtained by culturing host cells that have been transfected or transformed with the cloning vector in a suitable culture medium.

Suitable host/vector systems are available for propagation of nucleic acid sequences and the expression of peptides and proteins. Replicable plasmids, viral vectors, and host cells such as CHO, COS, insect, yeast and bacterial are well-known for use in genetic engineering and can be used herein.

The isolated nucleic acid molecules disclosed herein have various utilities, including their use as probes and primers as diagnostic reagents for identifying the presence of HMGI (Y)-LAMA4* nucleic acids in biological or other samples, and as agents for generating HMGI(Y)-LAMA4* polypeptides and HMGI(Y)-LAMA4* binding agents (agents such as antibodies which selectively bind to a HMGI(Y)-LAMA4* nucleic acid or to a HMGI(Y)-LAMA4* polypeptide) that can be used as reagents in diagnostic and therapeutic assays to identify the presence, absence, and/or amounts of a HMGI(Y)-LAMA4* nucleic acid or polypeptide in a biological or other sample. Thus, the foregoing HMGI(Y)-LAMA4* nucleic acids, polypeptides, and binding agents can be used, inter alia, in the diagnosis or treatment of conditions characterized by the expression or presence of HMGI(Y)-LAMA4* nucleic acid or polypeptide.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides (discussed below), the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Homologs and alleles of the HMGI(Y)-LAMA4* nucleic acids of the invention can be identified by conventional techniques. Thus, an aspect of the invention is those nucleic acid sequences which code for HMGI(Y)-LAMA4* polypeptides and which hybridize to a nucleic acid molecule selected from the group consisting of SEQ ID NO:1 and SEQ ID NO:2, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetraacetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of the HMGI(Y)-LAMA4* nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:2 and SEQ ID NO:3, respectively. In some instances sequences will share at least 50% nucleotide identity and/or at least 65% amino acid identity and in still other instances sequences will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for HMGI(Y)-LAMA4* related genes, such as homologs and alleles of HMGI(Y)-LAMA4*, a Southern blot may be performed using the foregoing conditions, together with a radioactive probe. After washing the membrane to which the DNA is finally transferred, the membrane can be placed against X-ray film or a phosphoimager plate to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating HMGI(Y)-LAMA4* polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of a nucleic acid molecule selected from the group consisting of SEQ ID NO:1 and SEQ ID NO:2. A unique fragment is one that is a 'signature' for the larger nucleic acid. For example, the unique fragment is long enough to assure that its precise sequence is not found in molecules within the human genome outside of the HMGI(Y)-LAMA4* nucleic acids defined above (and human alleles). Those of ordinary skill in the art may apply no more than routine procedures to determine if a fragment is unique within the human genome. The preferred unique fragments contain the HMGI (Y)-LAMA4* fusion sequence.

Unique fragments of HMGI(Y)-LAMA4* nucleic acids, however, exclude fragments completely composed of the nucleotide sequences of HMGI(Y) (SEQ ID NO:21) or LAMA4* (SEQ ID NO:7). Unique fragments of HMGI(Y)-LAMA4* nucleic acids also exclude fragments completely composed of the nucleotide sequences of a GenBank accession number or SEQ ID NOs listed in Tables 1a and 1b, or other previously published sequences as of the date of invention or the filing date of this application.

Unique fragments can be used as probes in Southern and Northern blot assays to identify such nucleic acids, or can be used in amplification assays such as those employing PCR. (See, e.g., the Examples.) As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or for determining binding of the polypeptide fragments, or for generating immunoassay components. Likewise, unique fragments can be employed to produce nonfused fragments of the HMGI (Y)-LAMA4* polypeptides, useful, for example, in the preparation of antibodies, immunoassays or therapeutic applications. Unique fragments further can be used as antisense molecules to inhibit the expression of HMGI(Y)-LAMA4* nucleic acids and polypeptides, respectively.

As will be recognized by those skilled in the art, the size of the unique fragment will depend upon its conservancy in the genetic code. Thus, some regions of SEQ ID NO:1, SEQ ID NO:2, and complements thereof will require longer segments to be unique while others will require only short segments, typically between 8 and 32 nucleotides long (e.g. 8, 9, 10, 11, 12, 13, 14, 15, 16, 17, 18, 19, 20, 21, 22, 23, 24, 25, 26, 27, 28, 29, 30, 31 and 32 bases) or more, up to the entire length of the disclosed sequences. As mentioned above, this disclosure intends to embrace each and every fragment of each sequence, beginning at the first nucleotide, the second nucleotide and so on, up to within about 8 nucleotides short of the end, and ending anywhere from nucleotide number 8, 9, 10 and so on for each sequence, up to the very last nucleotide, (provided the sequence is unique as described above). Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a HMGI(Y)-LAMA4* polypeptide, to decrease HMGI(Y)-LAMA4* function. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense oligonucleotides that selectively bind to the HMGI(Y)-LAMA4* fusion sequence are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 and/or SEQ ID NO:2, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., *Nat. Med.* 1(11):1116–1118, 1995. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID NO:2 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1 and/or SEQ ID NO:2. Similarly, antisense to allelic or homologous HMGI(Y)-LAMA4* cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding HMGI(Y)-LAMA4* polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Since, as demonstrated herein, the HMGI(Y)-LAMA4* fusion gene is found in neoplasias, the oncogenic role of the fusion gene is clear. Without wishing to be bound by any particular theory, there are several mechanisms by which the HMGI(Y)-LAMA4* oncoprotein may mediate transformation. One potential mechanism may stem from the fact that the LAMA4* EGF-like domain replaces the transcriptionally inactive HMGI(Y) carboxy terminus in the HMGI(Y) fusion cDNA. The HMGI(Y)-LAMA4* EGF-like domain may permit pathological recruitment of transcriptional regulators to the various AT-rich chromosomal regions that are HMGI(Y) A·T hook binding sites. A transcriptional regulatory function is particularly likely given similarities between the HMGI(Y)-LAMA4* fusion transcript and the mixed-lineage leukemia (MLL) oncogene.

Additional evidence supporting a transcription-related HMGI(Y)-LAMA4* oncogenic role is the relationship between motifs in this transcript and those involving HMGI-C in lipomas. HMGI(Y) and HMGI-C both encode nonhistone DNA-binding proteins that regulate gene expression through interactions with various transcription factors and through alterations in DNA conformation. None of the PCHs in this series had cytogenetic or molecular cytogenetic (FISH) rearrangement of the 12q15 HMGI-C region. Lipoma HMGI-C fusion transcripts result from juxtaposition of the three HMGI-C A·T hooks with transcriptional regulatory domains contributed by various translocation partners. See Schoenmakers et al., "Recurrent rearrangements in the high mobility group protein gene, HMGI-C, in benign mesenchymal tumors. *Nature Genet.* (1995) 10:436–444; and "Disruption of the architectural factor HMGI-C:DNA-binding A·T hook motifs fused in lipomas to distinct transcriptional regulatory domains," *Cell* (1995) 82:57–65. These observations establish a general mechanism of mesenchymal tumorigenesis involving fusion of high-mobility group DNA-binding domains with transcriptional regulatory sequences.

Since the HMGI(Y)-LAMA4* fusion oncogene is present in certain tumors, methods of assaying for the presence of the gene and/or its expression products provide methods for detection of such tumors. Assays which amplify and/or detect nucleic acids, peptides and proteins are well-known. Nucleic acid amplification techniques such the polymerase chain reaction (PCR) may be utilized to increase the number of nucleic acid units which encode all or portions of the HMGI(Y)-LAMA4* fusion protein based on the one or more preexisting copies contained in a tissue sample. Nucleic acid detection techniques based on hybridization of labeled probes, e.g., fluorescent in-situ hybridization (FISH), are capable of detecting small amounts of target sequences and are extremely useful herein.

PCR amplification of either DNA or mRNA encoding the HMGI(Y)-LAMA4* protein will increase detectable nucleic acid encoding HMGI(Y)-LAMA4* thereby providing a greater number of targets for detection with labeled probes. PCR techniques are well-known and described, for example, in Alberts et al., *Molecular Biology of the Cell*, 2nd ed., pp. 269–276 (1989), incorporated herein by reference. Briefly, PCR is performed by heating the sample to separate complementary nucleic acid strands which are then annealed to complementary primer oligonucleotides which serve as primers for DNA synthesis catalyzed by polymerase enzymes between the primers. Multiple cycles of PCR provide multiple copies of the target sequence as long as the target sequence was originally present in the sample.

Thus, in one aspect, the present invention provides a method for amplifying and detecting the presence of HMGI(Y)-LAMA4* fusion sequence in a sample by contacting the sample with at least first and second nucleic acid amplification primers such that the first nucleic acid amplification primer will hybridize to the nucleic acid sequence encoding HMGI(Y) or a complementary sequence thereto and the second nucleic acid amplification primer will hybridize to the nucleic acid sequence encoding LAMA4* or a complementary sequence thereto; amplifying the primed nucleic acid sequences in the sample; and detecting the presence of amplified nucleic acid sequence in the sample.

An example of an amplification primer for HMGI(Y) is 5'GGCTCAGTCATCTCAGTTGTGTA-3' (SEQ. ID NO. 9) and an amplification primer for LAMA4* is 5'-CCAGTGAGCAGAGTGACG-3' (SEQ. ID NO. 13). Examples of other primers are provided in the Examples, infra. It should be understood that amplification primers may be derived from any region of the HMGI(Y) sequence and any region of the LAMA4* sequence including intronic portions of genomic DNA. The target sequence for amplification can include genomic DNA or mRNA which encode all or unique fragments of the HMGI(Y)-LAMA4* nucleic acid sequence. It is apparent to those skilled in the art that other unique fragments derived from the HMGI(Y) and LAMA4* nucleic acid sequences or sequences complementary thereto can also be used as primers.

Detection of the HMGI(Y)-LAMA4* fusion sequence in a sample may be accomplished with any technique known to those with skill in the art. Since the HMGI(Y)-LAMA4* sequence is known in accordance with the present invention, existing detection techniques for amplified or unamplified nucleic acid such as in situ hybridization, Southern blotting of DNA, Northern blotting of RNA and PCR assays can be utilized. Immuno-histochemical detection methods are also utilizable herein. Size separation techniques such as electrophoresis may be utilized to resolve nucleic acids, peptides and/or proteins prior to institution of other detection techniques.

Nucleic acid probes for hybridization which are derived from HMGI(Y)-LAMA4* can be synthesized on an oligonucleotide synthesizer such as those commercially available from Applied Biosystems (California). DNA or RNA probes can also be derived by PCR using two primers from the HMGI(Y)-LAMA4* gene.

Thus, in accordance with the present invention, a HMGI(Y)-LAMA4* nucleic acid sequence (containing a HMGI(Y)-LAMA4* fusion sequence) contained within a sample can be detected by contacting the sample with first and second nucleic acid probes wherein the first probe hybridizes to the nucleic acid sequence encoding HMGI(Y) and the second probe hybridizes to the nucleic acid sequence encoding LAMA4*, and detecting the presence of a nucleic acid sequence within the sample that hybridizes to both the first and second probes. Alternatively, a single probe which spans the translocation fusion juncture can be utilized to detect the presence of the HMGI(Y)-LAMA4* fusion sequence in a sample. Thus, the presence of HMGI(Y)-LAMA4* fusion sequence can be detected by contacting the sample with a nucleic acid probe which hybridizes to the translocation fusion juncture of the HMGI(Y)-LAMA4* gene and detecting the presence of nucleic acid sequences in the sample which hybridize to the probe.

As is well-known in the art, probes utilized in detection of HMGI(Y)-LAMA4* encoding nucleic acids can be labeled directly by attaching a label to the probe or indirectly by causing a labeled binding partner to couple to the probe after hybridization. Examples of labels include fluorochromes such as fluorescein, Texas Red® and green fluorescent protein, enzymes such as horse radish peroxidase and radioactive isotopes. Signal amplification systems may also be utilized herein, e.g., avidin, streptavidin and biotin complexes or antibody hapten complexes. Such methods and systems are well known and are discussed generally, e.g., in Alberts et al., Molecular Biology of the Cell, 2nd ed., pp. 174 through 193, incorporated herein by reference. The availability of different labels provides convenient techniques for determining the presence of the HMGI(Y)-LAMA4* gene when, e.g., a first label is directed to the HMGI(Y) portion via a probe and a second different label is directed to the LAMA4* portion via a probe thus allowing visualization of different colors to confirm the presence of both portions in fused relationship. For example, a green fluorescent protein label appears as one color and Texas Red® appears as another color when using fluorescence, microscopy, spectrophotometry, fluorescent plate readers and flow sorters. Observation of distinct colors in close proximity confirms the presence of the oncogene.

According to yet another aspect of the invention, an isolated HMGI(Y)-LAMA4* polypeptide is provided. The isolated HMGI(Y)-LAMA4* polypeptide molecule is encoded by one or more HMGI(Y)-LAMA4* nucleic acid molecules of the invention. Preferably, the isolated HMGI(Y)-LAMA4* polypeptides of the invention are encoded by the nucleic acid molecule of SEQ ID NO:2 or a unique fragment thereof containing the HMGI(Y)-LAMA4* fusion sequence. In yet other embodiments, the isolated HMGI(Y)-LAMA4* polypeptides of the invention have the amino acid sequence of SEQ ID NO:3, or unique fragments thereof containing the HMGI(Y)-LAMA4* polypeptide fusion sequence. The isolated HMGI(Y)-LAMA4* polypeptides are of sufficient length to represent a sequence unique within the human genome.

In the preferred embodiments, the isolated HMGI(Y)-LAMA4* polypeptides are immunogenic and can be used to generate binding agents (e.g., binding polypeptides such as antibodies) for use in diagnostic and therapeutic applications. Such binding agents also are useful for detecting the presence, absence, and/or amounts of a HMGI(Y)-LAMA4* polypeptide in a sample such as a biological fluid or biopsy sample. Preferably, the HMGI(Y)-LAMA4* polypeptides that are useful for generating binding polypeptides are unique polypeptides and, therefore, binding of the antibody to a HMGI(Y)-LAMA4* polypeptide in a sample is selective for the HMGI(Y)-LAMA4* polypeptide.

A unique fragment of an HMGI(Y)-LAMA4* polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:3 and/or SEQ ID NO:4 will require longer segments to be unique while others will require only short segments, typically between 5 and 12 amino acids (e.g. 5, 6, 7, 8, 9, 10, 11 and 12 amino acids long or more, including each integer up to the full length, >1,000 amino acids long). Virtually any segment of SEQ ID NO:3 and/or SEQ ID NO:4, excluding the ones that share identity with it (e.g., the HMGI(Y) polypeptide, the LAMA4* polypeptide, and fragments of the foregoing, or other polypeptides published prior to the invention or application filing date) that is 9 or more amino acids in length will be unique.

One important aspect of a unique fragment is its ability to act as a signature for identifying the polypeptide. Another is its ability to provide an immune response in an animal. Those skilled in the art are well versed in methods for selecting unique amino acid sequences, typically on the basis of the ability of the unique fragment to selectively distinguish the sequence of interest from unrelated proteins. A comparison of the sequence of the fragment to those on known databases typically is all that is necessary.

The invention embraces variants of the HMGI(Y)-LAMA4* polypeptides described above. As used herein, a "variant" of a HMGI(Y)-LAMA4* polypeptide is a polypeptide which contains one or more modifications to the primary amino acid sequence of a HMGI(Y)-LAMA4* polypeptide. Modifications which create a HMGI(Y)-LAMA4* polypeptide variant are typically made to the nucleic acid which encodes the HMGI(Y)-LAMA4* polypeptide, and can include deletions, point mutations, truncations, amino acid substitutions and addition of amino acids or non-amino acid moieties to: 1) reduce or eliminate a functional activity of a HMGI(Y)-LAMA4* polypeptide; 2) enhance a property of a HMGI(Y)-LAMA4* polypeptide, such as protein stability in an expression system or the stability of protein-protein binding; 3) provide a novel activity or property to a HMGI(Y)-LAMA4* polypeptide, such as addition of an antigenic epitope or addition of a detectable moiety; or 4) to provide equivalent or better binding to a HMGI(Y)-LAMA4* polypeptide cognate molecule. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the HMGI (Y)-LAMA4* amino acid sequence. One of skill in the art will be familiar with methods for predicting the effect on protein conformation of a change in protein sequence, and can thus "design" a variant HMGI(Y)-LAMA4* polypeptide according to known methods. One example of such a method is described by Dahiyat and Mayo in Science 278:82–87, 1997, whereby proteins can be designed de novo. The method can be applied to a known protein to vary only a portion of the polypeptide sequence. By applying the computational methods of Dahiyat and Mayo, specific variants of a HMGI(Y)-LAMA4* calcium channel polypeptide can be proposed and tested to determine whether the variant retains a desired conformation.

Variants can include HMGI(Y)-LAMA4* polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a HMGI(Y)-LAMA4* polypeptide by eliminating proteolysis by proteases in an expression system.

Mutations of a nucleic acid which encodes a HMGI(Y)-LAMA4* polypeptide preferably preserve the amino acid reading frame of the coding sequence and, preferably, do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant HMGI(Y)-LAMA4* polypeptides) which are silent as to the amino acid sequence of the polypeptide, but which provide preferred codons for translation in a particular host. Still other mutations can be made to the noncoding sequences of a HMGI(Y)-LAMA4* gene or cDNA clone to enhance expression of the polypeptide.

The skilled artisan will realize that conservative amino acid substitutions may be made in HMGI(Y)-LAMA4* polypeptides to provide functionally equivalent variants of the foregoing polypeptides, i.e, the variants retain the functional capabilities of the HMGI(Y)-LAMA4* polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the HMGI(Y)-LAMA4* polypeptides include conservative amino acid substitutions of SEQ ID NO:3. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of HMGI(Y)-LAMA4* polypeptides, i.e., variants of HMGI(Y)-LAMA4* polypeptides which retain the function of the natural HMGI(Y)-LAMA4* polypeptides, are contemplated by the invention. Conservative amino-acid substitutions in the amino acid sequence of HMGI(Y)-LAMA4* polypeptides to produce functionally equivalent variants of HMGI (Y)-LAMA4* polypeptides typically are made by alteration of a nucleic acid encoding HMGI(Y)-LAMA4* polypeptides (e.g., SEQ ID NO:1 and SEQ ID NO:2). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a HMGI(Y)-LAMA4* polypeptide. The activity of functionally equivalent fragments of HMGI(Y)-LAMA4* polypeptides can be tested by cloning the gene encoding the altered HMGI(Y)-LAMA4* polypeptide into a bacterial or mammalian expression vector, introducing the vector into an appropriate host cell, expressing the altered HMGI(Y)-LAMA4* polypeptide, and testing for a functional capability of the HMGI(Y)-LAMA4* polypeptides as disclosed herein.

The HMGI(Y)-LAMA4* polypeptides may be purified from cells which naturally produce the polypeptide by chromatographic means or immunological recognition. Alternatively, an expression vector may be introduced into cells to cause production of the polypeptide. In another method, mRNA transcripts may be micro injected or otherwise introduced into cells to cause production of the encoded polypeptide. Translation of HMGI(Y)-LAMA4* mRNA in cell-free extracts such as the reticulocyte lysate system also may be used to produce HMGI(Y)-LAMA4* polypeptides. Those skilled in the art also can readily follow known methods for isolating HMGI(Y)-LAMA4* polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from HMGI(Y)-LAMA4* polypeptides. A dominant negative polypeptide is an inactive variant of a protein, which, by interacting with the cellular machinery, displaces an active protein from its interaction with the cellular machinery or competes with the active protein, thereby reducing the effect of the active protein. The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. See, e.g., U.S. Pat. No. 5,580,723 and Sambrook et al., 1989, *Molecular Cloning: A Laboratory Manual*, Second Edition, Cold Spring Harbor Laboratory Press. The skilled artisan then can test the population of mutagenized polypeptides for diminution in a selected activity and/or for retention of such an activity. Other similar methods for creating and testing dominant negative variants of a protein will be apparent to one of ordinary skill in the art.

According to another aspect of the invention, isolated HMGI(Y)-LAMA4* binding agents (e.g., binding polypeptides such as antibodies) which selectively bind to a HMGI(Y)-LAMA4* nucleic acid molecule or to a HMGI(Y)-LAMA4* polypeptide encoded by the isolated nucleic acid molecules of the invention are provided. Preferably, the isolated binding agents selectively bind to a nucleic acid having a sequence selected from the group consisting of SEQ ID NO:1 and SEQ ID NO:2; or to a polypeptide having a sequence selected from the group consisting of SEQ ID NO:3 and SEQ ID NO:4, or to unique fragments of the foregoing nucleic acids and polypeptides. In the preferred embodiments, the isolated binding polypeptides include antibodies and fragments of antibodies (e.g., Fab, F(ab)$_2$, Fd and antibody fragments which include a CDR3 region which binds selectively to a HMGI(Y)-LAMA4* nucleic acid or polypeptide). Preferably, the antibodies for human therapeutic applications are human antibodies.

As is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves binding polypeptides of numerous size and type that bind selectively to HMGI(Y)-LAMA4* polypeptides, and complexes containing HMGI(Y)-LAMA4* polypeptides. These binding polypeptides also may be derived from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. ml 3, fd, or lambda phage), displaying inserts from 4 to about 80 amino acid residues using conventional procedures. The inserts may represent, for example, a completely degenerate or biased array. One then can select phage-bearing inserts which bind to the HMGI(Y)-LAMA4* polypeptide or a complex containing a HMGI(Y)-LAMA4* polypeptide. This process can be repeated through several cycles of reselection of phage that bind to the HMGI(Y)-LAMA4* polypeptide or complex. Repeated rounds lead to enrichment of phage bearing particular sequences. DNA sequence analysis can be conducted to identify the sequences of the expressed polypeptides. The minimal linear portion of the sequence that binds to the HMGI(Y)-LAMA4* polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the HMGI(Y)-LAMA4* polypeptides. Thus, the HMGI(Y)-LAMA4* polypeptides of the invention, or a unique fragment thereof, or complexes of HMGI(Y)-LAMA4* can be used to screen peptide libraries, including phage display libraries, to identify and select peptide binding polypeptides that selectively bind to the HMGI(Y)-LAMA4* polypeptides of the invention. Such molecules can be used, as described, for screening assays, for purification protocols, for interfering directly with the functioning of HMGI(Y)-LAMA4* and for other purposes that will be apparent to those of ordinary skill in the art.

A HMGI(Y)-LAMA4* polypeptide, or a unique fragment thereof, also can be used to isolate naturally occurring, polypeptide binding partners which may associate with the HMGI(Y)-LAMA4* polypeptide in a cell. Isolation of binding partners may be performed according to well-known methods. For example, isolated HMGI(Y)-LAMA4* polypeptides can be attached to a substrate, and then a solution suspected of containing an HMGI(Y)-LAMA4* binding partner may be applied to the substrate. If the binding partner for HMGI(Y)-LAMA4* polypeptides is present in the solution, then it will bind to the substrate-bound HMGI(Y)-LAMA4* polypeptide. The binding partner then may be isolated. Other proteins which are binding partners for HMGI(Y)-LAMA4*, may be isolated by similar methods without undue experimentation.

The invention also provides novel kits which could be used to measure the levels of the nucleic acids of the invention, expression products of the invention or anti-HMGI(Y)-LAMA4* antibodies. In the case of nucleic acid detection, pairs of primers for amplifying HMGI(Y)-LAMA4* nucleic acids can be included. The preferred kits would include controls such as known amounts of nucleic acid probes, HMGI(Y)-LAMA4* epitopes (such as HMGI(Y)-LAMA4* expression products) or anti-HMGI(Y)-LAMA4* antibodies, as well as instructions or other printed material. In certain embodiments the printed material can characterize the risk of developing a disorder that is characterized by aberrant HMGI(Y)-LAMA4* polypeptide expression based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with a HMGI(Y)-LAMA4* polypeptide and a container containing labeled anti-human IgG antibodies. A well of the plate is contacted with, for example, serum, washed and then contacted with the anti-IgG antibody. The label is then detected. A kit embodying features of the present invention is comprised of the following major elements: packaging an agent of the invention, a control agent, and instructions. Packaging is a box-like structure for holding a vial (or number of vials) containing an agent of the invention. a vial (or number of vials) containing a control agent, and instructions. Individuals skilled in the art can readily modify packaging to suit individual needs.

In another aspect, HMGI(Y)-LAMA4* nucleic acid and the corresponding encoded polypeptides can be detected using antibodies, fragments of antibodies (embraced within the definition of antibodies, herein) and labels, and signal amplification techniques involving antibodies. Indeed, it is well-known to use immunochemical techniques to detect target nucleic acids and polypeptides and such techniques are well-suited for use herein. Antibodies which are immunoreactive to HMGI(Y)-LAMA4* nucleic acid or to the HMGI(Y)-LAMA4* polypeptide or to unique fragments of each are generated by known techniques, e.g., by immunization of animals such as mice with HMGI(Y)-LAMA4* nucleic acid or with HMGI(Y)-LAMA4* polypeptide or unique fragments thereof which include the translocation fusion juncture. Polyclonal and monoclonal antibodies may be generated using immortal cell lines for continuous production. Antibodies to HMGI(Y)-LAMA4* nucleic acid or to the HMGI(Y)-LAMA4* polypeptide or to unique fragments of each which include the translocation fusion juncture are then conjugated to labels such as those described above. Alternatively, if the so-called primary antibody is not labeled, it can be detected with a second labeled antibody which is immunoreactive with the first antibody.

Thus, HMGI(Y)-LAMA4* polypeptide or fragments thereof which include the translocation fusion juncture can be detected in a sample using antibodies by contacting the sample with one antibody which binds HMGI(Y) and another antibody which binds LAMA4* and detecting the presence of protein which binds to both antibodies. Alternatively, HMGI(Y)-LAMA4* or unique fragments thereof which include the translocation fusion juncture can be detected in a sample by contacting the sample with at least one antibody which binds to an epitope in the locus of the translocation fusion juncture and detecting the presence of proteins which bind to the antibody. Detection of such bound antibodies and proteins or peptides is accomplished by techniques well known to those skilled in the art. Use of hapten conjugates such as digoxigenin or dinitrophenyl is also well suited herein. Antibody/antigen complexes which form in response to hapten conjugates are easily detected by linking a label to the hapten or to antibodies which recognize the hapten and then observing the site of the label.

It should be understood that kits which include reagents that are used to detect HMGI(Y)-LAMA4* fusion sequence and peptides or proteins encoded thereby can be assembled which provide convenient access and use in clinical settings. For example, a kit can include a container which holds one or more amplification primers, a container which holds enzymes used for amplification, a container which holds washing solution(s), a container which holds detection reagents, and a sample well. Alternatively, a kit can include a container which holds one or more antibodies directed to HMGI(Y) or the peptide or protein encoded thereby, a container which holds one or more antibodies directed to LAMA4* or the peptide or protein encoded thereby, a container which holds washing solution(s), a container which holds detection reagents, and a sample well. Alternatively, antibody contained in the container can be directed to an epitope in the locus of the translocation fusion juncture of HMGI(Y)-LAMA4* or the protein encoded thereby. It is also contemplated that a kit can include a container having one or more labeled or unlabeled probes capable of hybridizing to the HMGI(Y) gene or corresponding mRNA, a container having one or more labeled or unlabeled probes capable of hybridizing to the LAMA4* encoding portion gene or corresponding mRNA and, if the probe is unlabeled, a container having a labeled specific binding partner of the probe or to a recognition site on the probe, e.g., biotinylated probe, a container which holds washing solution(s), a container which holds detection reagents, and a sample well. Alternatively, a kit may contain a single probe which is capable of hybridizing to the locus of the translocation fusion juncture of HMGI(Y)-LAMA4* along with other suitable components such as washing solution and the like.

Examples of detection reagents include radiolabeled probes, enzymatic labeled probes (horse radish peroxidase, alkaline phosphatase), and affinity labeled probes (biotin, avidin, or streptavidin). For antibodies, examples of detecting reagents include, but are not limited to, labeled secondary antibodies, or, if the primary antibody is labeled, the chromophoric, enzymatic, or antibody binding reagents which are capable of reacting with the labeled antibody. The antibodies, primers and nucleic acid probes described herein can readily be incorporated into one of the established kit formats which are well known in the art.

Molecular characterization of HMGI(Y)-LAMA4* nucleic acid and the polypeptide encoded thereby allows production of therapeutic agents which selectively locate and/or destroy cells containing the fusion nucleic acid, its mRNA or corresponding polypeptide. For example, radiolabeled antibodies or fragments of antibodies which bind to the nucleic acid, mRNA or corresponding polypeptide can be injected into a patient suspected of having tumors containing HMGI(Y)-LAMA4* nucleic acids or corresponding polypeptides. Since the injected radiolabeled antibodies or antibody fragments collect in the area of cells having the nucleic acid, mRNA or corresponding polypeptide, such cells may be detected and localized within a patient by observing the locus of radioactivity generated by the antibodies or fragments of antibodies. Methods of tumor localization using radiolabeled antibodies or fragments of antibodies (radioimmunodetection) are well-known in the art. See, e.g., U.S. Pat. No. 4,348,376 incorporated herein by reference.

Cells containing the HMGI(Y)-LAMA4* fusion sequence or polypeptide encoded thereby may be selectively destroyed by conjugating toxins to antibodies or fragments of antibodies which bind to the nucleic acid or polypeptide. Thus, by injecting a toxin/antibody or toxin/antibody fragment conjugate into a patient having HMGI(Y)-LAMA4* fusion nucleic acid or polypeptide encoded thereby, wherein the antibody or antibody fragment is directed to HMGI(Y)-LAMA4* fusion nucleic acid or polypeptide encoded thereby, cells containing the fusion nucleic acid or polypeptide are preferentially destroyed by the toxin which binds to the locus of the fusion nucleic acid or polypeptide. In this manner, surgical resection of tumors may be avoided. Use of toxin conjugated antibodies or toxin conjugated antibody fragments is well-known in the art. See, e.g., U.S. Pat. No. 4,671,958, incorporated herein by reference. Examples of suitable toxins include those derived from diphtheria toxin, ricin and the like.

In another aspect, production of HMGI(Y)-LAMA4* polypeptide is inhibited by addition of antisense RNA to cells which produce HMGI(Y)-LAMA4* protein. Thus, DNA is introduced into cells producing HMGI(Y)-LAMA4* protein, the DNA being configured to produce antisense RNA that is complementary to mRNA that encodes HMGI(Y)-LAMA4*. Such antisense mRNA hybridizes with the sense mRNA made by HMGI(Y)-LAMA4* thereby inhibiting synthesis of HMGI(Y)-LAMA4* protein. Methods of producing antisense mRNA and use thereof for inhibition of protein sequences are well-known in the art. Indeed, expression vectors are constructed to produce high levels of antisense RNA in transfected cells. This approach has led to reduced expression of oncogenes in exemplary instances whereby antisense oncogene constructs have reverted the growth properties of tumor cells to near normal, slowed their growth or induced apoptosis. See Watson et al., *Recombinant DNA*, 2d ed., 1992. For example, Philadelphia human chronic myelogenous leukemia (CML) cells that contain the BCR/ABL translocation have been eradicated using antisense molecules targeted to this oncogene in clinical, pre-clinical, and laboratory settings. *J. Nat'l. Cancer Inst*. Vol. 89, No. 2, Jan. 15, 1997. A similar approach is employed according to the HMGI(Y)-LAMA4* oncogene. For example, tumor cells harboring the HMGI(Y)-LAMA4* oncogene are treated ex vivo with antisense molecules directed at the oncogene mRNA to induce apoptosis thereby purging the tumor cells.

In another aspect, ribozymes, which are catalytic RNA sequences that cleave specific RNA molecules, are used to disrupt translation involving the HMGI(Y)-LAMA4* oncogene. Several studies have demonstrated that ribozymes can be employed to inhibit oncogene expression, cell growth or induce apoptosis in tumor cell lines. U.S. Pat. No, 5,635,385 to Leopold, et al., incorporated herein by reference, describes a therapeutic method for the treatment of a leukemia patient resulting from a chromosomal translocation (BCR/ABL) using a ribozyme that cleaves the oncogene mRNA and inhibits the expression of the gene. A similar approach is employed according to the present invention using a synthetic ribozyme targeted to the HMGI(Y)-LAMA4* oncogene.

In yet another aspect, triplex forming oligonucleotides and RNA-DNA hybrid technology is used to disrupt or otherwise modify the HMGI(Y)-LAMA4* oncogene. Deoxyoligonucleotides and RNA-DNA hybrids are designed to bind directly to duplex DNA in a sequence-specific manner. Once bound, they can either prevent transcription, alter a specific base sequence to correct a mutation or mutagenize a sequence to disrupt function of the gene or its regulatory elements. This has been achieved in a number of model systems. See, e.g.,*J. Biol. Chem*. Vol. 271, No. 24 (1996). A similar approach is employed according to the present invention using triplex forming oligonucleotides and RNA-DNA hybrids targeted to the HMGI(Y)-LAMA4* oncogene or its regulatory elements. For example, triplex forming oligonucleotides are designed to bind to a relatively polypurine stretch of nucleotides adjacent to the target area. The oligonucleotide is configured to serve as a carrier of DNA for the induction of recombination to insert a mutation or carry a DNA interacting agent (e.g., Mitomycin C) to directly mutagenize either the coding region or the regulatory region of the HMGI(Y)-LAMA4* oncogene to disable its function or induce apoptosis.

It is also contemplated that the HMGI(Y)-LAMA4* oncogene may be used in gene transfer studies by the transfer of the genomic DNA or cDNA of the gene into target cells to serve as a transforming agent for the production of vaccines, induction of apoptosis or other indications. In one aspect, the HMGI(Y)-LAMA4* oncogene is used to transfect nonneoplastic cells such as mesenchymal and/or epithelial cells and study the effects on those cells such as transformation. Additionally, transgenic animals may be generated which contain the HMGI(Y)-LAMA4* oncogene which are useful in studying transformation effects of HMGI(Y)-LAMA4*. Methods of creating transgenic animals are well known in the art. For example, U.S. Pat. No. 4,873,191, incorporated herein by reference, describes genetic transformation of zygotes. Following such procedures, the HMGI(Y)-LAMA4* oncogene is microinjected into the nucleus of a zygote which is then allowed to undergo differentiation and development into a mature organism. Transgenic animals such as mice or pigs will have somatic and germ line cells containing the HMGI(Y)-LAMA4* oncogene. Such animals are useful as in vivo models for certain malignant syndromes and allow for the further development and testing of treatment modalities.

The invention also discloses the nucleic acid and predicted amino acid sequence for a novel gene, referred to herein as "LAMA4*". The summary of the invention provides various aspects of the invention which are based upon the discovery of this novel gene. Accordingly, the invention provides isolated LAMA4* nucleic acid molecules, unique fragments thereof, expression vectors containing the foregoing, host cells containing the foregoing, isolated LAMA4* polypeptides, and unique fragments thereof. The invention also provides isolated binding agents which selectively bind such LAMA4* nucleic acids and LAMA4* polypeptides, including antibodies, and pharmaceutical compositions containing the foregoing molecules. The terms, "unique fragments" and "isolated" as defined in reference to the HMGI(Y)-LAMA4* nucleic acid and polypeptides have the same meanings as defined in reference to the LAMA4* nucleic acid and polypeptides disclosed herein. In general, each of the methods described above in reference to the HMGI(Y)-LAMA4* invention can be applied to the LAMA4* invention by, for example, substituting the LAMA4* nucleic acids and polypeptides for the HMGI(Y)-LAMA4* nucleic acids and polypeptides in the above-described methods. For example, binding agents that selectively bind to the LAMA4* nucleic acid or polypeptide can be used for diagnostic applications, in vivo or in vitro, to identify the presence and/or amount of a LAMA4* nucleic acid or expression product thereof in a subject or in a biological sample obtained from a subject. Accordingly, the compositions of the invention that are directed to the LAMA4* nucleic acid or LAMA4* polypeptide can be used, inter alia, in the diagnosis or treatment of conditions that are characterized by the aberrant expression levels and/or the presence of a LAMA4* nucleic acid or polypeptide.

TABLE 1a

SEQ ID NO:1 Blast Sequences

AC005907, M23619, M23616, L17131, Z98048, M23618, AJ223042, M23617, M23615, X14957, M23614, X14958, AB010101, AL034393, AE001445, AC002476, AB007881, Z83318, AC003037, AC006299, AF104355, AC005116, AC005698, Z66567, AC003075, AF106579, Z72723, Y11689, AC003103, U64573, AC005660, Z49067, AL032649, Z72722, AB022215, X81058, AE001563, AB016890, U76419, U39718, AF001393, Z47067, X61520, AA000331, AI048383, AA276105, AA016936, AA027546, AI326714, AA958507, W20716, AA154530, AA288429, AA163325, AA008773, AI049437, AA265324, C76891, AA444412, AA475195, AA510541, AA237828, W21247, W55995, C21259, AA227577, AA434446, AA227918, AI192906, AA398384, AI343487, AI042404, AA525786, AI127653, AA775784, N94756, W56285, AI417600, AA360621, N94804, W31373, W39693, AI382064, AA767042, H73348, AA610829, AA814967, N99526, AA776981, AI073992, R32831, AI084766, AA625345, AI343815, R42438, H95429, W58640, AA480128, N33264, AA311175, AA071303, AA280966, T97413, AA262798, AA171430, AA406390, T71731, N35678, T71749, AA173840, AA209371, AI004016, AI138340,

TABLE 1a-continued

SEQ ID NO:1 Blast Sequences

H24636, AA204866, AI322150, AI008005, AU006894, AU010408, AR008092, I09646

TABLE 1b

SEQ ID NO:2 Blast Sequences

X14958, U77706, M23616, M23615, Z99289, X14957, M23617, M23618, M23614, J04179, L17131, M23619, AC005907, X91171, S78569, Z63068, U69176, Y09827, U59865, Z81055, AC002536, AF065393, AC004207, AB010886, AC004722, AC004208, M23288, AF006264, AF100657, X86451, AF058287, AL023575, U30471, Z82976, U41109, Y08890, AF015825, L14837, AF107256, U73649, Z77132, U15277, AA726426, AA870235, AA656860, AA171172, AA221244, W20906, W58869, AA003742, AA014417, W75534, AA538243, AA285405, W13051, W08773, AA637322, AA517318, AA153313, AA589214, AA600393, AI151784, AA560420, AA125182, AA183512, W09706, AA790253, AI343487, AI042404, AI080221, AA496983, AI290678, AI004016, AA173840, AI192906, AI417600, AI381809, AA662357, AA075815, AA262782, AA625345, AA890585, AA948275, AA434214, W56285, AA171615, N93512, W55995, AA227918, AA227577, AA916507, AA171430, AA480128, AI075663, AA209371, AA262798, AA767093, AA071303, AA204866, AA311175, AA074694, AA434446, AA570097, AA670089, AA648523, AA206006, W21247, AA810888, R56442, AI161028, AI004017, AI144303, AA566278, AI332228, AA605569, AI331535, AA550482, AA754500, AU010992, AA550658, AA550664, D71633, AU008160, AA751940, C54183, AU003674, I07376, E08652, I07373, I38435, I15009, AI6121, I08188, I38450, I15001, I96212, I08187

TABLE 2

SEQ ID NO:7 Blast Sequences

U77706, S78569, X91171, Y14240, Z99289, Y09827, U59865, U69176, AJ233828, AF007134, AB007648, AF013614, Z92772, S70041, Y09798, U51994, AA616866, AA087640, AA560420, AA183512, AI413428, AA790253, C76362, AA596643, W53650, AA144625, AA144777, AA062249, C76365, AA427267, C76285, C76248, AA980204, C76131, AI118581, C76360, AA451492, AA183782, AA098220, C76286, AA670089, AI367995, AA428919, AA418641, AA122294, AI367594, AA062778, W45521, AA418579, AI392677, AA570097, AI082045, AI221117, AA193258, AI143546, AA490581, AI394384, AA115950, AI207032, W45534, AA912774, AA917351, AA742686, AA568653, AA025549, AA025650, AA302471, AA063480, AI275596, AI244017, AA040665, AA362996, R89638, R73339, AA180294, AA127051, AA704474, AA903234, AI307820, R43519, AA047238, AI188596, AI310379, F03612, W42454, AA852319, R44329, R43617, C06407, AA470766, AA744244, AI363085, H22258, AI360415, AI280218, AI184373, AA770660, AA634185; AA676517, AI382436, H97620, AI097534, AA703997, AA534691, AA704466, AI122580, AI299912, T66165, AI367570, R23696, R72872, H10396, AI075192, AA854705, N27450, R53572, T33643, AI128390, N90493, AA055469, AI074308, AA731330, AA397935, AA461059, AI146611, AI180160, AI407377, AI007983, AI407399, AA819423, AA996623, AA891919, AI102937, AI011600, AU030783, AU031635, AA940715, AI292516, AI257368, D47096, AA817332,, I16616, I96212, I08188, E08652, I38435, I07373, E13813, I07376, I38450, I08187, AI6121, A52568, I51993

The following examples are included for purposes of illustration and are not intended to limit the scope of the invention. The Examples and additional illustrative figures originally were disclosed in the U.S. Provisional Patent Application Ser. No. 60/076,401, filed Feb. 28, 1998, to which priority is claimed, the entire contents of which are incorporated herein by reference.

EXAMPLES

Tissue Culture and Cytogenetic Analysis

Surgical hamartoma specimens were processed for cytogenetic analysis immediately after excision. All specimens were minced with scalpels, disaggregated with collagenase, and cultured as described in Fletcher et al., "Diagnostic relevance of clonal cytogenetic aberrations in malignant soft-tissue tumors," N. Engl. J. Med. (1991) 324:436:442, herein incorporated by reference. Metaphase harvesting, slide making, and trypsin-Giemsa staining were also as described in Fletcher et al., Id. Metaphase cells were harvested from all cases within 8 days after establishing the primary cultures.

Mapping 6p21 Breakpoints by Fluorescence in Situ Hybridization (FISH)

Chromosome band 6p21 breakpoints in 4 PCHs were mapped by FISH with Centre d'Etudes du Polymorphisme Humain mega-YAC clones. Centre d'Etudes du Polymorphisme Humain mega-YAC walks were guided by publicly available contig data from the Whitehead/Massachusetts Institute of Technology Genome Center World-Wide Web site. PAC and YAC clones containing HMGI(Y) were isolated by screening the corresponding libraries with gene-specific primers 5'GGCTCAGTCATCTCAGTTGTGTA-3' (SEQ ID NO:9) (forward) and 5'GAACCCCAAGAGAAGGTAACA-3'(SEQ ID NO:10) (reverse). DNAs isolated from P1 6995 plasmid (commercially available from Genome Systems, St. Louis, Mo.), PAC, and YAC clones were biotin labeled by random octamer priming as described in Xiao et al., "Novel fluorescence in situ hybridization approaches in solid tumors: characterization of frozen specimens, touch preparations, and cytological preparations," Am. J. Pathol. (1995) 147:896–904, herein incorporated by reference. Plasmid DNAs were digoxigenin labeled by nick translation. Solutions and conditions for hybridization and post-hybridization washing were as described in Xiao et al., Id. All probes were visualized using fluorescein avidin (Vector Laboratories, Burlingame, Calf.) or rhodamine anti-digoxigenin (Boehringer Mannheim, Indianapolis, Ind.) with counterstaining by 0.1 µg/ml 4,6-diamidino-2-phenylindole-dihydrochloride. Images were captured using an Oncor FISH/comparative genomic hybridization image analysis system, commercially available from Oncor, Inc., Gaithersburgh, Md.

YACs 769_f_10(1050 kb) and 808_h_5(730 kb), both containing D6S439 sequence tagged sites (GenBank), were centromeric to the 6p21 breakpoint in each PCH, whereas YAC 921_g_3(330 kb), containing D6S273 sequence tagged sites (GenBank), was telomeric to the breakpoints. D6S273 was 160 centirays from 6pter by radiation hybrid mapping, whereas RP_S10_2, another sequence tag site in YAC 769_f_10, was 167 cR from 6pter. These map locations defined a PCH 6p21 breakpoint region flanked by sequence tag sites approximately 2 megabases apart. Mega-YAC 755_c_6(550 kb) contained HMGI(Y) and mapped between D6S439 and D6S273. FISH evaluations with this YAC were carried out against metaphase cells from the four PCHs with cytogenetic 6p21 rearrangements (90-288, 92-100, 93-562, and 93-701; Table 3 below). YAC 755_c_6 spanned the 6p21 breakpoints in each of these cases.

TABLE 3

Cytogenetic Aberrations and 6p21 Breakpoint Mapping in Five Hamartomas

| Case | Cytogenetics | 6p21 Breakpoint |
|---|---|---|
| 90–288 | t(6;14)(p21;q24) | 3' to HMGI(Y) |
| 91–32 | t(6;14)(p21;q24) | ND |
| 92–100 | t(6;10)(p21;q22) | 5' to HMGI(Y) |
| 93–562 | inv(6)(p21q21) | HMGI(Y) intron 7 |
| 93–701 | (6;10)(p21;q24) | 3' to HMGI(Y) |

ND, not determined

Expression Studies

Figure 2A:
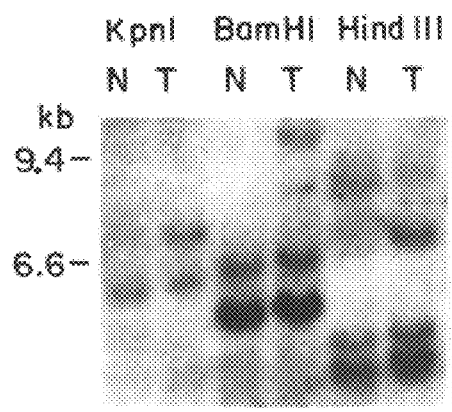
FIG. 2A depicts a photograph of a Southern blot analysis of PCH 93-562 (T) and non-neoplastic fibroblasts (N).

Southern blot hybridization with HMGI(Y) complete-sequence cDNA revealed aberrant restriction fragments in PCH 93-562. This case contains a chromosome 6 pericentromeric inversion, inv(6)(p21q21). Four other PCHs with cytogenetic aberrations at 7p21 lacked aberrant HMGI(Y) restriction fragments. The intragenic HMGI(Y) breakpoint in 93-562 was localized to the exon 7/intron 7/exon 8 region by reprobing the Southern blot with a genomic clone (FIG. 2A). More particularly, FIG. 2A depicts Southern blot analysis of PCH 93-562 (T) and nonneoplastic fibroblasts (N). Hybridization was with a genomic clone containing exon 7, intron 7, and exon 8 of HMGI(Y). Rearranged fragments are seen in KpnI, BamHI and HindIII digested 93-562 DNA.

Figure 2B:
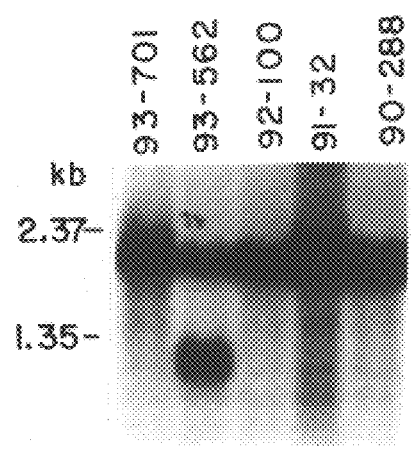
FIG. 2B depicts a photograph of a Northern blot analysis of five PCHs by hybridization with HMGI(Y) cDNA.

Northern blots prepared with total RNA from quiescent PCH cells revealed an abnormal ~1-kb transcript in PCH 93-562 (FIG. 2B). More particularly, total RNA was isolated from five PCHs that had been grown to confluence in p150 dishes and then held for 5 days with no evidence of further cell division.

Northern blots were prepared by electrophoresis of 20 µg of total RNA per lane in formaldehyde/1% agarose gels, followed by transfer to Hybond N membranes (Amersham, Arlington Heights, Ill.). All probes were labeled with $^{32}$P by random priming according to Feinberg et al. "A technique for radiolabeling DNA restriction endonuclease fragments to high specific activity," Anal. Biochem. (1983) 132:6–13, incorporated herein by reference. Hybridization and washing were performed according to standard protocols according to Sambrook J. et al., Molecular Cloning: A Laboratory Manual, Plainville, N.Y., Cold Spring Harbor Laboratory Press (1989), incorporated herein by reference, and blots were rehybridized with a full-length β-actin cDNA probe to confirm equal lane loading. As can be seen from FIG. 2B, abundant HMGI(Y) transcripts of normal size (1.9 kb) were present in the remaining PCHs. FIG. 2B depicts Northern blot analysis of the five PCHs by hybridization with an HMGI(Y) cDNA. The 1.9 kb normal transcripts are seen in each case, and a 1 kb aberrant transcript is seen in 93-562.

HMGI(Y) expression was then re-evaluated by mRNA ISH against paraffin-embedded histological sections from PCHs 92-100 and 93-562. mRNA ISH was performed on 4-µm paraffin-embedded PCH sections using digoxigenin-labeled sense and antisense HMGI(Y) riboprobes. Hybridizations were carried out using a Ventana GenII ISH system (Ventana Medical Systems, Tucson, Ariz.). Riboprobe preparation, using T3 and T7 RNA polymerases, and hybridization conditions were as described in Galaktionov et al., "CDC25 phosphatases as potential human oncogenes," Science (1995) 269:1575–1577 incorporated herein by reference. Detection was with alkaline-phosphatase anti-digoxigenin and nitroblue tetrazolium and 5-bromo-4-chloro-3-indolyl-phosphate as substrate. HMGI(Y) transcripts were abundant in uncultured adipose, chondroid, and primitive, mesenchymal cells from PCHs 92-100 and 93-562, whereas transcripts were undetectable in normal fibroblasts from the pulmonary parenchyma surrounding these hamartoma nodules.

Characterization of HMGI(Y) -LAMA4* Fusion Transcripts

A potential HMGI(Y) fusion gene was evaluated by rapid amplification of cDNA 3' ends (3' RACE) from PCH 93-562. Total RNA was isolated from 93-562 cells, and RT-PCR was performed with HMGI(Y) exon 5 and oligo(dT) primers. Total RNA (5 μg) was reverse transcribed in a 20-μl reaction using murine leukemia virus reverse transcriptase (Perkin Elmer, Norwalk, Conn.) with an oligo(dT) primer, 5'-CCAGTGAGCAGAGTGACGAGGACTCGAGCTCAAG-CTTTTTTTTTTTTTTTTT-3' (SEQ ID NO:11) according to Frohman "Rapid amplification of complementary DNA ends for generation of full-length complementary DNAs: thermal RACE," *Methods Enzymol.* (1993) 218:340–356, incorporated herein by reference. A 1-μl aliquot of cDNA was amplified using an HMGI(Y) sense primer (5'-AGAAGGGAAGATGAGTGAGTC-3') (SEQ ID NO:12) in a 50-μl polymerase chain reaction (PCR) reaction (10 mmol/L tris/HCL, pH 8.3, 50 mmol/L KCl, 1.5 mmol/L $MgCl_2$, 200 μmol/L each dNTP, 10% dimethylsulfoxide, and 2.5 U of Taq polymerase) denaturation at 95° C. for 2 minutes and then 5 cycles of linear amplification at 94° C. for 30 seconds, 58° C. for 30 seconds, and 72° C. for 1.5 seconds. Adaptor primer $Q_0$ (5'-CCAGTGAGCAGAGTGACG-3') (SEQ ID NO:13) was then added to the reaction, followed by another 25 cycles of amplification. An aliquot of the reaction was reamplified with nested HMGI(Y) sense (5'-GAAAAGGACGGCA-CTGA-3') (SEQ ID NO:14) and $Q_1$ adaptor (5'-GAGGACTCGAGCTCAAGC-3') (SEQ ID NO:15) primers using the PCR conditions described above. The reamplified PCR product was electrophoresed, gel purified, subcloned, and sequenced.

The 3' RACE reaction yielded a 711-bp PCR product that was subcloned. Sequence analysis of this 3' RACE product revealed in-frame fusion of a 454-bp novel sequence immediately after exon 7 of HMGI(Y). BLASTN sequence searching demonstrated that the 102 nucleotides immediately 3' to the fusion breakpoint were identical to nucleotides 196 and 297 from the laminin α4 chain (LAMA4) cDNA. The 3' end of the fusion sequence was novel, however, with no homologies to laminin family members or other known genes (FIG. 3). FIG. 3 depicts LAMA4* cDNA and deduced amino acid sequence for LAMA4* wherein cysteines in the EGF-like domain are circled and putative polyadenylation signals are underlined. The vertical line indicates the location of the breakpoint in the PCH 93-562 HMGI(Y)/LAMA4* fusion cDNA. Two LAMA4* cDNAs have identical coding sequences but differ at the 5' untranslated region (5'UTR-A and 5'UTR-B). The dashed box defines regions of nucleotide identity with LAMA4. Regions of identity are 437 bp for LAMA4*/5'UTR-A (LAMA4 nucleotides—140 to 297) and 487 bp for LAMA4*/5'UTR-B (LAMA44 nucleotides—190 to 297).

Additional studies, described below, indicate that the HMGI(Y) fusion transcript partner results from LAMA4 alternative splicing. This LAMA4 alternative splicing transcript proved to be 1 kb in size, whereas a previously described LAMA4 transcript was 6.2 kb. Nomenclature convention suggested by Airenne et al., "Structure of the human laminin 2 chain gene (LAMC2): alternative splicing with different tissue distribution of two transcripts," Genomics (1996) 32:54–64, was used to refer to the short alternative splicing product as LAMA4*.

The HMGI(Y)-LAMA4* fusion transcript in PCH 93-562 was confirmed by RT-PCR using primers from exon 5 of HMGI(Y) and from 3' LAMA4* sequences, i.e., (initial denaturation at 95° C. for 2 minutes, followed by 30 cycles at 94° C. for 30 seconds, 58° C. seconds, and 72° C. for 30 seconds) using primers from the novel LAMA4* sequence (5'-CAAGGCAGATACAGAGGTCTT-3') (SEQ ID NO:16) and from HMGI(Y) (5'-AAGTGCCAACACCTAAGAGAC-3') (SEQ ID NO:17). A product of the predicted size was amplified from 93-562 but not from control, nonneoplastic, fibroblasts.

The 5' end of the LAMA4* cDNA was next isolated by 5' RACE from placental poly A+RNA. Oligonucleotide primers specific for 3' LAMA4* sequences were employed in conjunction with 5' adaptor primers. 5' LAMA4* cloning was performed using a Clontech Marathon cDNA amplification kit (Clontech, Palo Alto, Calif.). First-strand cDNA was synthesized from 1 μg of placental poly(A)+RNA using Moloney murine leukemia virus RT. Second-strand cDNA was then synthesized and adaptor ligated according to the manufacturer's protocol. Adaptor-ligated cDNA was amplified using a LAMA4*-specific primer (5'GCCCTGGCTTCTCTGGCTCCCTGA-3') (SEQ ID NO:18) and adaptor primer AP1 from the kit. Conditions were as follows: initial denaturation at 95° C. for 2 minutes, 94° C. for 30 seconds, 68° C. for 3 minutes for 30 cycles. These PCR products were reamplified using a nested LAMA4* primer (5'-GGCTCCCTGAGAGCTGAGAATGAACG-3') (SEQ ID NO:19) and adaptor primer AP2. Conditions were identical to first-round amplification except that the number of cycles was 20. The final PCR product was electrophoresed, transferred to a Hybond N membrane (Amersham), and hybridized with an LAMA4* oligonucleotide probe internal to the RACE primers (5'-CAGGATACTGTGTGACTACTGACG-3') (SEQ ID NO:20). The confirmed LAMA4* RACE product was gel purified, subcloned, and sequenced.

Two amplification products measuring 641 and 744 bp were obtained. Derivation of the two 5' RACE products from LAMA4* was confirmed by Southern blot analysis using an internal oligonucleotide probe from the 3' end of the LAMA4* cDNA. Sequence analysis revealed that both 5' RACE cDNAs contained identical LAMA4* coding sequences with divergence in the 5' untranslated region (FIG. 3). Coexpression of the two LAMA4* cDNAs was next demonstrated both in nonneoplastic ST91-249 fibroblast cells and poly A+placental RNA. This was accomplished by RT-PCR with oligonucleotide primers specific for each of he two LAMA4* 5' ends in conjunction with a LAMA4* 3' end primer. Sequences corresponding in size to those predicted from the two LAMA4* cDNAs were amplified both from fibroblast and placental RNAs. BLAST searches established identity between LAMA4* and LAMA4 cDNAs at a region including the first 99 amino acids of the corresponding proteins encoded by these sequences (FIG. 3).

Whereas the 6.2-kb LAMA4 cDNA encodes three cysteine-rich epidermal growth factor (EGF)-like domains, the LAMA4* cDNAs encode only a single EGF-like domain (FIG. 3). The HMGI(Y)-LAMA4* cDNA results from fusion of the three HMGI(Y) DNA-binding domains with the LAMA4* EGF-like domain. FIG. 1 depicts an ideogram of chromosome 6 inversion in PCH 93-562. Inversion breakpoints at 6p21 and 6q21 result in fusion of HMGI(Y) AT book DNA-binding domains (DBD) with LAMA4* EGF-like domain. As discussed above, expression of fusion transcript 5'-HMGI(Y)-LAMA4*-3' was readily demonstrable by RT-PCR and Northern blot analyses in PCH 93-562. However, a predicted 1.8-kb transcript from the reciprocal aspect of the chromosome 6 inversion, 5'-LAMA4*-HMGI(Y)-3', was not detected after hybridizations of 93-562 Northern blots with LAMA4* 5'-end cDNA probes.

HMGI(Y)-region PCH Chromosome Breakpoint Localizations

HMGI(Y) transcriptional orientation was determined by FISH with a 5.7-kb 5' promoter/enhancer region probe in PCH 93-562 metaphase cells. Whereas an HMGI(Y) P1 clone spanned the 93-562 inversion breakpoint, the HMGI(Y) promoter/enhancer region probe 5.7 kb hybridized telomeric to this breakpoint. Hence, HMGI(Y) transcriptional orientation is toward the centromere, and LAMA4 transcriptional orientation, by extrapolation, is centromeric (FIG. 1). Chromosome band 6p21 breakpoints were then localized in three PCHs that had both normal HMGI(Y) Southern blot studies (FIG. 2A) and metaphase cells available for FISH (Table 3). The PCH 93-701 breakpoint was centromeric to HMGI(Y) PAC, P1, and plasmid clones, whereas the PCH 90-288 translocation breakpoint was crossed by HMGI(Y) PAC clone 7387 (130 kb) but centromeric to HMGI(Y) PI clone 6995 (90 kb). The PCH 92-100 6p21 translocation breakpoint was crossed by HMGI(Y) PAC and P1 clones but was telomeric to the 5.7-kb HMGI(Y) 5' promoter/enhancer region plasmid clone. These studies demonstrate that 93-701 and 90-288 breakpoints are 3' to HMGI(Y), whereas the 92-100 breakpoint is 5' to HMGI(Y).

LAMA4* Chromosomal Sublocalization and Expression

Chromosomal sublocalization of the LAMA4* cDNA was established by radiation hybrid mapping using a primer pair that amplified a 113-bp genomic sequence. Mapping against the Genebridge 4 radiation hybrid panel according to Walter et al., "A method for constructing radiation hybrid maps of whole genomes," Nature Genet. (1994) 7:22–28, localized LAMA4* 1.82 centirays from D6S418 (lod<3.0) in chromosome band 6q21. CEPH mega-YACs containing LAMA4* cDNA sequences were then identified by PCR screening. Mega-YACs 811_d_4, 770_g_4, and 856_g_2 from a Whitehead Institute contig according to Hudson, et al.,"An STS-based map of the human genome," Science (1995) 270:1945–1954, contained the LAMA4* cDNA, and FISH mapping revealed that each of these YACs crossed the chromosome 6 inversion breakpoint in PCH 93-562. The shared 5' end of the LAMA4/LAMA4* cDNAs also localized to the same three mega-YACs, whereas the 3' end of the LAMA4 cDNA mapped centromeric to mega-YAC 856_g_2 in a region of the contig defined by overlap of mega-YACs 852_d_6, 767_h_6, 811_d_4, and 770_g_4. These mapping studies confirm the direction of LAMA4 gene transcription as centromeric.

Figure 4:
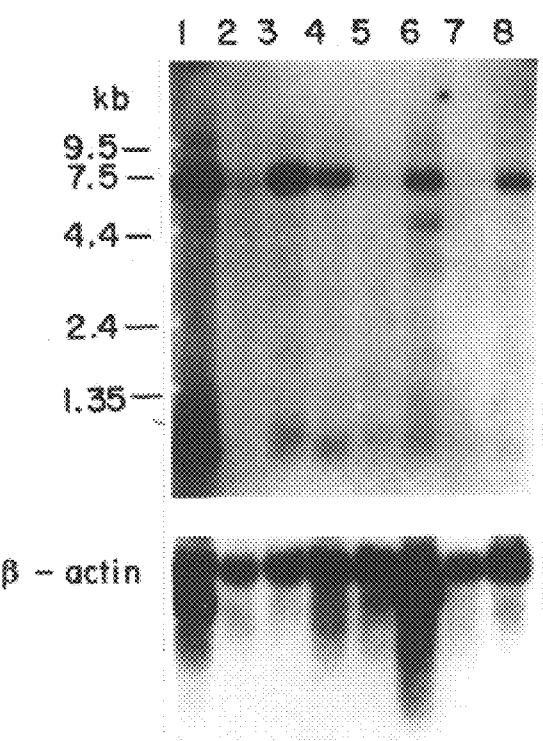
FIG. 4 depicts a photograph of a multiple tissue Northern blot hybridized with LAMA4* cDNA clones containing sequences shared with LAMA4.

LAMA4* expression was evaluated by hybridizing a human multiple tissue northern blot (Clontech) with pooled probes from LAMA4* cDNA 5' and 3' ends. FIG. 4 depicts the multiple tissue Northern blot hybridized with LAMA4* cDNA clones containing sequences shared with LAMA4. Lane 1, heart; lane 2, brain; lane 3, placenta; lane 4, lung; lane 5, liver; lane 6, skeletal muscle; lane 7, kidney; lane 8, pancreas. Abundant LAMA4 6.2-kb transcripts are seen in heart, placenta, lung, skeletal muscle, and pancreas. The LAMA4* 1-kb transcript is abundant only in heart and is present at lower levels in placenta, lung, liver, and skeletal muscle.

It will be understood that various modifications may be made to the embodiments disclosed herein. Therefore, the above description should not be construed as limiting, but merely as exemplifications of preferred embodiments. Those skilled in the art will envision other modifications within the scope of the claims appended hereto.

All references, patents, and patent applications disclosed herein are incorporated by reference in their entirety.

What is claimed is:

1. An isolated nucleic acid sequence comprising a sequence selected from the group consisting of GGCAGAC-CCAAAAAACTGAAATGCAATGCT (SEQ ID NO:1) and SEQ ID NO:2.

2. A replicable vector comprising a nucleic acid of claim 1.

3. A host cell comprising a replicable vector including a nucleic acid of claim 1.

4. A method of identifying the presence of an HMGI(Y)-LAMA4* fusion sequence in a sample comprising:

analyzing the sample for the presence of a nucleic acid sequence containing the nucleic acid sequence of claim 1.

5. The method of claim 4, wherein the method of identifying the presence of an HMGI(Y)-LAMA4* fusion sequence in a sample comprises:

contacting the sample with at least two nucleic acid amplification primers, wherein the first nucleic acid amplification primer is capable of hybridizing to the HMGI(Y) nucleic acid sequence and the second nucleic acid amplification primer is capable of hybridizing to the LAMA4* nucleic acid sequence;

amplifying the primed sequences in the sample which hybridize to the two primers; and detecting the presence of amplified nucleic acid sequences in the sample which contains the HMGI(Y)-LAMA4* sequence.

6. The method of claim 4, wherein the method of identifying the presence of an HMGI(Y)-LAMA4* fusion sequence in a sample comprises:

contacting the sample with at least two nucleic acid probes, wherein the first nucleic acid probe is capable of hybridizing to a nucleic acid sequence encoding HMGI(Y) and the second nucleic acid probe is capable of hybridizing to a nucleic acid sequence encoding LAMA4*; and detecting the presence of a nucleic acid sequence in the sample which hybridizes to both the first and the second nucleic acid probes.

7. The method of claims 4, wherein the method of identifying the presence of an HMGI(Y)-LAMA4* fusion sequence in a sample comprises:

contacting the sample with a nucleic acid probe which is capable of hybridizing to the locus of the junction between the HMGI(Y) portion and LAMA4* portion of the HMGI(Y)-LAMA4* fusion sequence; and detecting the presence of a nucleic acid sequence in the sample which hybridizes to the probe.

* * * * *

SEQUENCE LISTING

<160> NUMBER OF SEQ ID NOS: 22

<210> SEQ ID NO 1
<211> LENGTH: 30
<212> TYPE: DNA
<213> ORGANISM: Homo Sapiens

<400> SEQUENCE: 1
ggcagaccca aaaaactgaa atgcaatgct         30

<210> SEQ ID NO 2
<211> LENGTH: 920
<212> TYPE: DNA
<213> ORGANISM: Homo Sapiens

<400> SEQUENCE: 2
ggccggtgct gcgctcctct aattgggact ccgagccggg gctatttctg gcgctggccg    60
ggctccaaga aggcatccgc atttgctacc agcggcggcc gcggcggagc caggccggtc   120
ctcagcgccc agcaccgccg ctcccggcaa cccggagcgc gcaccgcagc cggcggccga   180
gctcgcgcat cccagccatc actcttccac ctgctcctta gagaagggaa gatgagtgag   240
tcgagctcga agtccagcca gcccttggcc tccaagcagg aaaaggacgg cactgagaag   300
cggggccggg gcaggccgcg caagcagcct ccgaaggagc ccagcgaagt gccaacacct   360

-continued

```
aagagacctc ggggccgacc aaagggaagc aaaaacaagg gtgctgccaa gacccggaaa      420
accaccacaa ctccaggaag gaaaccaagg ggcagaccca aaaaactgaa atgcaatgct      480
ggattctttc acaccctgtc gggagaatgt gtgccctgcg actgtaatgg caattccaac      540
gagtgtttgg acggctcagg atactgtgtg actactgacg gagaagaccc aggttttca      600 gcttctaccc tatcgttcat tctcagctct cagggagcca gagaagccag ggctccaaca      660
tgaacacttc ttgtagctca ctgtcatgac cagtgtttca gtcagttctt tcaggttgcc      720
tgacttacct catttctctc atttcctgta agcaaccaaa aataaaaggc tttctttat      780 ttcattttgt cttatttgc ttttatcttg aaggcatata agacctctgt atctgccttg      840
ttcaccttca actgcttcta attcttcctc aattccagtg tccaatgtca atttgaaatt      900
aaaatttaca gactgatttt                                                 920
```

<210> SEQ ID NO 3
<211> LENGTH: 143
<212> TYPE: PRT
<213> ORGANISM: Homo Sapiens

<400> SEQUENCE: 3

```
Met Ser Glu Ser Ser Lys Ser Ser Gln Pro Leu Ala Ser Lys Gln
 1               5                  10                  15

Glu Lys Asp Gly Thr Glu Lys Arg Gly Arg Gly Arg Pro Arg Lys Gln
            20                  25                  30

Pro Pro Lys Glu Pro Ser Glu Val Pro Thr Pro Lys Arg Pro Arg Gly
        35                  40                  45

Arg Pro Lys Gly Ser Lys Asn Lys Gly Ala Ala Lys Thr Arg Lys Thr
    50                  55                  60

Thr Thr Thr Pro Gly Arg Lys Pro Arg Gly Arg Pro Lys Lys Leu Lys
65                  70                  75                  80

Cys Asn Ala Gly Phe Phe His Thr Leu Ser Gly Glu Cys Val Pro Cys
                85                  90                  95

Asp Cys Asn Gly Asn Ser Asn Glu Cys Leu Asp Gly Ser Gly Tyr Cys
            100                 105                 110

Val Thr Thr Asp Gly Glu Asp Pro Gly Phe Ser Ala Ser Thr Leu Ser
        115                 120                 125

Phe Ile Leu Ser Ser Gln Gly Ala Arg Glu Ala Arg Ala Pro Thr
    130                 135                 140
```

<210> SEQ ID NO 4
<211> LENGTH: 10
<212> TYPE: PRT
<213> ORGANISM: Homo Sapiens

<400> SEQUENCE: 4

```
Gly Arg Pro Lys Lys Leu Lys Cys Asn Ala
 1               5                  10
```

<210> SEQ ID NO 5
<211> LENGTH: 899
<212> TYPE: DNA
<213> ORGANISM: Homo Sapiens

<400> SEQUENCE: 5

```
cttctggagc ccttggaggg gctccaaact gagaggggag ggaagaccgc aggaaaggcg       60
gacctcagtg tctgaaaagc cagcttagag tgggagggcc tgggagtaga agctgctggt     120
```

```
tgcgcacgca cctcgggata ctgcacacgg agaggaggga aaataagcga ggcaccgccg    180
caccacgcgg agacctacgg agacccacag cgcccgagcc ctggaagagc actactggat    240
gtcagcggaa aaatggcttt gagctcagcc tggcgctcgg ttctgcctct gtggctcctc    300
tggagcgctg cctgctcccg cgccgcgtcc ggggacgaca acgcttttcc ttttgacatt    360
gaagggagct cagcggttgg caggcaagac ccgcctgaga cgagcgaacc ccgcgtggct    420
ctgggacgcc tgccgcctgc ggccgagaaa tgcaatgctg gattctttca caccctgtcg    480
ggagaatgtg tgccctgcga ctgtaatggc aattccaacg agtgtttgga cggctcagga    540
tactgtgtga ctactgacgg agaagaccca ggttttttcag cttctaccct atcgttcatt    600
ctcagctctc agggagccag agaagccagg gctccaacat gaacacttct tgtagctcac    660
tgtcatgacc agtgtttcag tcagttcttt caggttgcct gacttacctc atttctctca    720
tttcctgtaa gcaaccaaaa ataaaaggct ttctttttatt tcattttgtc ttattttgct    780
tttatcttga aggcatataa gacctctgta tctgccttgt tcaccttcaa ctgcttctaa    840
ttcttcctca attccagtgt ccaatgtcaa tttgaaatta aaatttacag actgatttt     899

<210> SEQ ID NO 6
<211> LENGTH: 1002
<212> TYPE: DNA
<213> ORGANISM: Homo Sapiens

<400> SEQUENCE: 6
caaactgaat cctgctttaa ttcaagcttg tggagaacaa agtcctacag aaacattcca     60
cagaattttc tggaaaagag ggatcacaac aaccctgtaa aaggtgagaa aggaagccag    120
gacagcgcag tccccagtcc cgaacggcca gggagaggag gtggcctagc gctggcgggg    180
ctcaccccaa tccgtctgcc ttttgatgcc gtactctgct ggttgcgcac gcacctcggg    240
atactgcaca cggagaggag ggaaaataag cgaggcaccg ccgcaccacg cggagaccta    300
cggagaccca cagcgcccga gccctggaag agcactactg gatgtcagcg gagaaatggc    360
tttgagctca gcctggcgct cggttctgcc tctgtggctc ctctggagcg ctgcctgctc    420
ccgcgccgcg tccggggacg acaacgcttt tccttttgac attgaaggga gctcagcggt    480
tggcaggcaa gaccccgcctg agacgagcga accccgcgtg gctctgggac gcctgccgcc    540
tgcggccgag aaatgcaatg ctggattctt tcacaccctg tcgggagaat gtgtgccctg    600
cgactgtaat ggcaattcca acgagtgttt ggacggctca ggatactgtg tgactactga    660
cggagaagac ccaggttttt cagcttctac cctatcgttc attctcagct ctcagggagc    720
cagagaagcc agggctccaa catgaacact tcttgtagct cactgtcatg accagtgttt    780
cagtcagttc tttcaggttg cctgacttac ctcatttctc tcatttcctg taagcaacca    840
aaataaaaag ctttcttttt atttcatttt gtcttatttt gcttttatct tgaaggcata    900
taagacctct gtatctgcct tgttcacctt caactgcttc taattcttcc tcaattccag    960
tgtccaatgt caatttgaaa ttaaaattta cagactgatt tt                      1002

<210> SEQ ID NO 7
<211> LENGTH: 529
<212> TYPE: DNA
<213> ORGANISM: Homo Sapiens

<400> SEQUENCE: 7
ctgctggttg cgcacgcacc tcgggatact gcacacgag aggagggaaa ataagcgagg     60
caccgccgca ccacgcggag acctacggag acccacagcg cccgagccct ggaagagcac    120
```

-continued

```
tactggatgt cagcggagaa atggcttga gctcagcctg gcgctcggtt ctgcctctgt    180
ggctcctctg gagcgctgcc tgctcccgcg ccgcgtccgg ggacgacaac gcttttcctt    240
ttgacattga agggagctca gcggttggca ggcaagaccc gcctgagacg agcggaaccc    300
cgcgtggctc tgggacgcct gccgcctgcg gccgagaaat gcaatgctgg attctttcac    360
accctgtcgg gagaatgtgt gccctgcgac tgtaatggca attccaacga gtgtttggac    420
ggctcaggat actgtgtgac tactgacgga gaagacccag ttttttcagc ttctacccta    480
tcgttcattc tcagctctca gggagccaga gaagccaggg ctccaacat                529
```

<210> SEQ ID NO 8
<211> LENGTH: 129
<212> TYPE: PRT
<213> ORGANISM: Homo Sapiens

<400> SEQUENCE: 8

```
Met Ala Leu Ser Ser Ala Trp Arg Ser Val Leu Pro Leu Trp Leu Leu
 1               5                  10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val Thr Thr Asp Gly Glu Asp Pro Gly Phe Ser Ala Ser Thr
            100                 105                 110

Leu Ser Phe Ile Leu Ser Ser Gln Gly Ala Arg Glu Ala Arg Ala Pro
        115                 120                 125

Thr
```

<210> SEQ ID NO 9
<211> LENGTH: 23
<212> TYPE: DNA
<213> ORGANISM: Homo Sapiens

<400> SEQUENCE: 9

```
ggctcagtca tctcagttgt gta                                            23
```

<210> SEQ ID NO 10
<211> LENGTH: 21
<212> TYPE: DNA
<213> ORGANISM: Homo Sapiens

<400> SEQUENCE: 10

```
gaacccaag agaaggtaac a                                               21
```

<210> SEQ ID NO 11
<211> LENGTH: 52
<212> TYPE: DNA
<213> ORGANISM: Homo Sapiens

<400> SEQUENCE: 11

```
ccagtgagca gagtgacgag gactcgagct caagcttttt ttttttttt tt             52
```

```
<210> SEQ ID NO 12
<211> LENGTH: 21
<212> TYPE: DNA
<213> ORGANISM: Homo Sapiens

<400> SEQUENCE: 12
agaagggaag atgagtgagt c                                        21

<210> SEQ ID NO 13
<211> LENGTH: 18
<212> TYPE: DNA
<213> ORGANISM: Homo Sapiens

<400> SEQUENCE: 13
ccagtgagca gagtgacg                                            18

<210> SEQ ID NO 14
<211> LENGTH: 17
<212> TYPE: DNA
<213> ORGANISM: Homo Sapiens

<400> SEQUENCE: 14
gaaaaggacg gcactga                                             17

<210> SEQ ID NO 15
<211> LENGTH: 18
<212> TYPE: DNA
<213> ORGANISM: Homo Sapiens

<400> SEQUENCE: 15
gaggactcga gctcaagc                                            18

<210> SEQ ID NO 16
<211> LENGTH: 21
<212> TYPE: DNA
<213> ORGANISM: Homo Sapiens

<400> SEQUENCE: 16
caaggcagat acagaggtct t                                        21

<210> SEQ ID NO 17
<211> LENGTH: 21
<212> TYPE: DNA
<213> ORGANISM: Homo Sapiens

<400> SEQUENCE: 17
aagtgccaac acctaagaga c                                        21

<210> SEQ ID NO 18
<211> LENGTH: 24
<212> TYPE: DNA
<213> ORGANISM: Homo Sapiens

<400> SEQUENCE: 18
gccctggctt ctctggctcc ctga                                     24

<210> SEQ ID NO 19
<211> LENGTH: 26
<212> TYPE: DNA
<213> ORGANISM: Homo Sapiens

<400> SEQUENCE: 19
ggctccctga gagctgagaa tgaacg                                   26
```

-continued

```
<210> SEQ ID NO 20
<211> LENGTH: 24
<212> TYPE: DNA
<213> ORGANISM: Homo Sapiens

<400> SEQUENCE: 20
caggatactg tgtgactact gacg                                              24

<210> SEQ ID NO 21
<211> LENGTH: 1875
<212> TYPE: DNA
<213> ORGANISM: Homo Sapiens

<400> SEQUENCE: 21
ggccggtgct gcgctcctct aattgggact ccgagccggg gctatttctg gcgctggccg        60
ggctccaaga aggcatccgc atttgctacc agcggcggcc gcggcggagc caggccggtc       120
ctcagcgccc agcaccgccg ctcccggcaa cccggagcgc gcaccgcagc cggcggccga       180
gctcgcgcat cccagccatc actcttccac ctgctcctta gagaagggaa gatgagtgag       240
tcgagctcga agtccagcca gcccttggcc tccaagcagg aaaaggacgg cactgagaag       300
cggggccggg gcaggccgcg caagcagcct ccgaaggagc ccagcgaagt gccaacacct       360
aagagacctc ggggccgacc aaagggaagc aaaaacaagg gtgctgccaa gacccggaaa       420
accaccacaa ctccaggaag gaaaccaagg ggcagaccca aaaaactgga gaggaggaa        480 gaggagggca tctcgcagga gtcctcggag gaggagcagt gacccatgcg tgccgcctgc       540
tcctcactgg aggagcagct tccttctggg actggacagc tttgctccgc tcccaccgcc       600 ccgcccctt cccaggccc accatcacca ccgcctctgg ccgccacccc catcttccac         660
ctgtgccctc accaccacac tacacagcac accagccgct gcagggctcc catgggctga      720
gtggggagca gttttcccct ggcctcagtt cccagctccc ccgcccacc cacgcataca       780 cacatgccct cctggacaag gctaacatcc cacttagccg cacccctgcac ctgctgcgtc      840 cccactccct tggtggtggg gacattgctc tctgggcttt tggtttgggg gcgccctctc       900
tgcctccttc actgttccct ctggcttccc atagtggggc ctgggagggt tcccctggc       960 cttaaaaggg gcccaagccc atctcatcct ggcacgccct actccactgc cctggcagca      1020
gcaggtgtgg ccaatggagg ggggtgctgg cccccaggat tccccagcc aaactgtctt      1080 tgtcaccacg tggggctcac ttttcatcct tccccaactt ccctagtccc cgtactaggt      1140
tggacagccc ccttcggcta caggaaggca ggaggggtga gtcccctact ccctcttcac      1200
tgtggccaca gccccttgc cctccgcctg ggatctgagt acatattgtg gtgatggaga       1260
tgcagtcact tattgtccag gtgaggccca agagccctgt ggccgccacc tgaggtgggc      1320
tggggctgct cccctaaccc tactttgctt ccgccactca gccatttccc cctcctcaga      1380 tgggcacca ataacaagga gctcaccctg cccgctccca accccctcc tgctcctccc       1440 tgccccccaa ggttctggtt ccattttcc tctgttcaca aactacctct ggacagttgt       1500
gttgtttttt gttcaatgtt ccattcttcg acatccgtca ttgctgctgc taccagcgcc      1560
aaatgttcat cctcattgcc tcctgttctg cccacgatcc cctcccccaa gatactcttt      1620
gtggggaaga ggggctgggg catggcaggc tgggtgaccg actacccag tcccagggaa       1680 ggtgccctgc ccctaggatg ctgcagcaga gtgagcaagg gggcccgaat cgaccataaa      1740
gggtgtaggg gccacctcct cccctgttc tgttggggag gggtagccat gatttgtccc      1800
```

-continued

```
agcctggggc tccctctctg gtttcctatt tacagttact tgaataaaaa aaatatcctt      1860
ttctggaaaa aaaaa                                                       1875

<210> SEQ ID NO 22
<211> LENGTH: 96
<212> TYPE: PRT
<213> ORGANISM: Homo Sapiens

<400> SEQUENCE: 22

Met Ser Glu Ser Ser Ser Lys Ser Ser Gln Pro Leu Ala Ser Lys Gln
1               5                   10                  15

Glu Lys Asp Gly Thr Glu Lys Arg Gly Arg Gly Arg Pro Arg Lys Gln
                20                  25                  30

Pro Pro Lys Glu Pro Ser Glu Val Pro Thr Pro Lys Arg Pro Arg Gly
            35                  40                  45

Arg Pro Lys Gly Ser Lys Asn Lys Gly Ala Ala Lys Thr Arg Lys Thr
        50                  55                  60

Thr Thr Thr Pro Gly Arg Lys Pro Arg Gly Arg Pro Lys Lys Leu Glu
65                  70                  75                  80

Lys Glu Glu Glu Glu Gly Ile Ser Gln Glu Ser Ser Glu Glu Glu Gln
                85                  90                  95
```